(12) United States Patent
Mihan et al.

(10) Patent No.: US 7,619,090 B2
(45) Date of Patent: Nov. 17, 2009

(54) MONOCYCLOPENTADIENYL COMPLEXES COMPRISING A CONDENSED HETEROCYCLE

(75) Inventors: Shahram Mihan, Lugwigshafen (DE); Ilya Nifant'ev, Moscow (RU)

(73) Assignee: Basell Polyolefine GmbH, Wesseling (DE)

( * ) Notice: Subject to any disclaimer, the term of this patent is extended or adjusted under 35 U.S.C. 154(b) by 210 days.

(21) Appl. No.: 10/489,023

(22) PCT Filed: Sep. 10, 2002

(86) PCT No.: PCT/EP02/10117
§ 371 (c)(1), (2), (4) Date: Mar. 9, 2004

(87) PCT Pub. No.: WO03/024982
PCT Pub. Date: Mar. 27, 2003

(65) Prior Publication Data
US 2004/0242880 A1    Dec. 2, 2004

(30) Foreign Application Priority Data
Sep. 14, 2001 (DE) ................. 101 45 453

(51) Int. Cl.
C07D 215/38 (2006.01)
(52) U.S. Cl. .................. 546/153; 546/276.4; 546/268.1
(58) Field of Classification Search ................. 546/153, 546/2, 276.4, 268.1
See application file for complete search history.

(56) References Cited

U.S. PATENT DOCUMENTS

| | | |
|---|---|---|
| 3,242,150 A | 3/1966 | Scoggin |
| 3,248,179 A | 4/1966 | Norwood |
| 5,068,489 A | 11/1991 | Edwards et al. |
| 5,506,184 A | 4/1996 | Kissin et al. |
| 5,637,660 A | 6/1997 | Nagy et al. |
| 6,177,376 B1 | 1/2001 | Fritze et al. |
| 6,211,311 B1 | 4/2001 | Wang et al. |
| 6,255,418 B1 | 7/2001 | Jolly et al. |
| 6,291,386 B1 | 9/2001 | Wang |
| 6,417,302 B1 | 7/2002 | Bohnen |
| 6,437,161 B1 | 8/2002 | Mihan et al. |
| 6,451,724 B1 | 9/2002 | Nifant'ev et al. |
| 6,518,379 B1 | 2/2003 | Jungling et al. |
| 6,583,237 B1 | 6/2003 | Imuta et al. |
| 6,589,905 B1 | 7/2003 | Fischer et al. |
| 6,812,305 B2 | 11/2004 | Kristen et al. |
| 6,924,248 B2 | 8/2005 | Mihan et al. |
| 6,930,190 B2 | 8/2005 | Nitant'eu et al. |
| 6,936,666 B2 | 8/2005 | Mihan et al. |
| 7,087,686 B2 | 8/2006 | Briovsek et al. |
| 7,094,724 B2 | 8/2006 | Fraaije et al. |
| 7,238,818 B2 | 7/2007 | Ewen et al. |

| | | |
|---|---|---|
| 2003/0148877 A1 | 8/2003 | Nifant'ev et al. |
| 2003/0176275 A1 | 9/2003 | Fraaije et al. |

FOREIGN PATENT DOCUMENTS

| | | |
|---|---|---|
| DE | 197 10615 | 9/1998 |
| DE | 10017660 | 10/2001 |
| DE | 10028432 | 12/2001 |
| WO | 97/36937 | 10/1977 |
| WO | 91/09882 | 7/1991 |
| WO | 96/00243 | 1/1996 |
| WO | 98/22468 | 5/1998 |
| WO | WO 98/22486 | 5/1998 |
| WO | 98/27124 | 6/1998 |
| WO | 98/37106 | 8/1998 |
| WO | 98/40419 | 9/1998 |
| WO | 99/06414 | 2/1999 |
| WO | 99/24446 | 5/1999 |
| WO | 00/05277 | 2/2000 |
| WO | 00/31090 | 6/2000 |
| WO | WO 00/43426 | 7/2000 |
| WO | WO 00/71593 | 11/2000 |
| WO | 01/09148 | 2/2001 |
| WO | 01/12641 | 2/2001 |
| WO | 01/44318 | 6/2001 |
| WO | WO 01/40330 | 6/2001 |
| WO | 01/47393 | 7/2001 |
| WO | 01/53360 | 7/2001 |
| WO | WO 01/77187 | 10/2001 |
| WO | WO 01/96417 | 12/2001 |
| WO | WO 01/96418 | 12/2001 |
| WO | 02/31001 | 4/2002 |
| WO | WO 03/014107 | 2/2003 |
| WO | WO 03/042253 | 5/2003 |

OTHER PUBLICATIONS

J.Organ.Chem. 369(1989)359-370, Wiesenfeldt et al., 359-370.
J.Am.Chem.Soc. 1998,120,4049-4050, Small et al.
Lettau,Chemie der Heterocyclen, 1$^{st}$ Ed. VEB, Weinheim, 1979, 17-27.
"Metalorganic catalysts for synthesis and polymerisation", Springer Verlag 1999, Ewen et al.
Jutzi, U. Siemeling, J. Orgmet. Chem., 1995, 500, 175-185.
Enders et al., Chem. Ber., 1996, 129, 459-463.
Chem Rev. 92, 1992, 965-994, Halterman.
S. Strauss, Chem. Rev., 1993, 93, 927-942.
Organometallics 2000, 19, 388-402, Doehring et al.
Chemical Reviews, vol. 100, 2000, Michl, Editor.
G. Britovsek, Chem. Commun., p. 849-850 (1998).
B. Wakefield, Organomagnesium Methods in Organic Synthesis, Academic Press, p. 96 (1995).
Office Action mailed Dec. 30, 2005 (U.S. Appl. No. 10/489,387)
Reply mailed Jun. 27, 2006 (U.S. Appl. No. 10/489,387).
Office Action mailed Sep. 7, 2006 (U.S. Appl. No. 10/489,387) Reply mailed Mar. 1, 2007 (U.S. Appl. No. 10/489,387).
Office Action mailed May 21, 2007 (U.S. Appl. No. 10/489,387).

*Primary Examiner*—D. Margaret Seaman
(74) *Attorney, Agent, or Firm*—William R Reid

(57) ABSTRACT

Monocyclopentadienyl complexes containing a cyclopentadienyl system comprising at least one fused heterocycle and at least one uncharged donor which can be used in catalyst systems for the polymerization or copolymerization of olefins.

8 Claims, No Drawings

MONOCYCLOPENTADIENYL COMPLEXES COMPRISING A CONDENSED HETEROCYCLE

The present invention relates to monocyclopentadienyl complexes in which the cyclopentadienyl system comprises at least one fused heterocycle and at least one uncharged donor and to a catalyst system comprising at least one of the monocyclopentadienyl complexes.

In addition, the invention relates to the use of the catalyst system for the polymerization or copolymerization of olefins and to a process for preparing polyolefins by polymerization or copolymerization of olefins in the presence of the catalyst system, and to polymers obtained in this way.

Organotransition metal compounds such as metallocene complexes are of great interest as catalysts for olefin polymerization because they make it possible to synthesize polyolefins which are not obtainable using conventional Ziegler-Natta catalysts. For example, such single site catalysts lead to polymers having a narrow molar mass distribution and a uniform comonomer content. Apart from bis(cyclopentadienyl) compounds, use is also made of "constrained geometry" catalyts. These are usually titanium complexes in the oxidation state 4 containing only one cyclopentadienyl system which is connected via a bridge to an anionic amide which is likewise bound to the titanium center.

WO 98/22486 describes bis(cyclopentadienyl) complexes in which one or two of the cyclopentadienyl systems contain one or more fused-on heterocycles.

WO 98/37106 discloses catalyst systems comprising transition metal complexes having at least one cyclopentadienyl ligand containing a fused-on heterocycle and a further cyclopentadienyl ligand or an anionic donor.

In J. Org. Chem. 1996, 61, 7230-7231, Fu et al. describe ferrocene complexes in which one of the cyclopentadienyl rings contains a fused-on pyridine ring.

It is an object of the present invention to find transition metal complexes based on cyclopentadienyl ligands containing a fused-on heterocycle which are suitable for the polymerization of olefins.

We have found that this object is achieved by a monocyclopentadienyl complex which comprises the following structural feature of the formula $(HCp)Y_nM$, where the variables have the following meanings:

HCp is a cyclopentadienyl system containing at least one fused heterocycle,

Y is a substituent which is bound to HCp and comprises at least one uncharged donor containing an atom of group 15 or 16 of the Periodic Table, M is a metal of group 3, 4, 5, 6, 7, 8, 9 or 10 of the Periodic Table, and n is 1, 2 or 3.

Furthermore, a catalyst system comprising the monocyclopentadienyl complexes of the invention, the use of the catalyst system for the polymerization or copolymerization of olefins and a process for preparing polyolefins by polymerization or copolymerization of olefins in the presence of the catalyst system and also polymers obtainable in this way have been found.

The monocyclopentadienyl complexes of the present invention comprise $(HCp)Y_nM$ as structural element, where the variables have the above meanings. Further ligands can therefore be bound to the metal atom M. The number of further ligands depends, for example, on the oxidation state of the metal atom. Possible further ligands do not include further cyclopentadienyl systems. Suitable ligands are monoanionic and dianionic ligands as are described, for example, for X. In addition, Lewis bases such as amines, ethers, ketones, aldehydes, esters, sulfides or phosphines can also be bound to the metal center M.

HCp is a cyclopentadienyl system containing at least one fused heterocycle. In the following, cyclopentadientyl is a $C_5$ ring system having 6 π electrons, where one of the carbon atoms may also be replaced by nitrogen or phosphorus, preferably phosphorus. Preference is given to using a $C_5$ ring system without replacement by a heteroatom. At least one heterocycle containing at least one atom of group 15 or 16 of the Periodic Table is fused onto this basic cyclopentadienyl skeleton. In the present context, fused-on means that the heterocycle and the cyclopentadienyl skeleton share two atoms, preferably carbon atoms. Preference is given to cyclopentadienyl systems HCp of the formula (F-I)

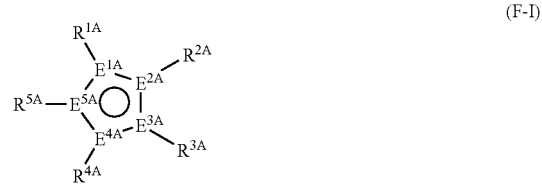

(F-I)

where the variables have the following meanings:

$E^{1A}$-$E^{5A}$ are each carbon or at most one $E^{1A}$ to $E^{5A}$ is phosphorus or nitrogen, preferably phosphorus, $R^{1A}$-$R^{5A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $SiR^{6A}_3$, where the organic radicals $R^{1A}$-$R^{5A}$ may also be substituted by halogens and two vicinal radicals $R^{1A}$-$R^{5A}$ may also be joined to form a five- or six-membered ring, with the proviso that at least two vicinal radicals $R^{1A}$-$R^{5A}$ are joined to form a heterocycle which contains at least one atom from group 15 or 16 of the Periodic Table, and an $R^{1A}$-$R^{5A}$ may be Y and $R^{6A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl radical and 6-20 carbon atoms in the aryl radical and two geminal radicals $R^{6A}$ may also be joined to form a five- or six-membered ring.

In preferred cyclopentadienyl systems HCp, all $E^{1A}$ to $E^{5A}$ are carbon.

At least two vicinal radicals $R^{1A}$-$R^{5A}$ form a heterocycle which contains at least one atom from group 15 or 16 of the Periodic Table, preferably nitrogen, phosphorus, oxygen and/or sulfur, particularly preferably nitrogen and/or sulfur. Preference is given to heterocycles having a ring size of 5 or 6 ring atoms. Examples of 5-membered ring heterocycles, which may contain from one to four nitrogen atoms and/or a sulfur or oxygen atom as ring members in addition to carbon atoms, are furan, thiophene, pyrrole, isoxazole, 3-isothiazole, pyrazole, oxazole, thiazole, imidazole, 1,2,4-oxadiazole, 1,2,5-oxadiazole, 1,3,4-oxadiazole, 1,2,3-triazole and 1,2,4-triazole. Examples of 6-membered heteroaryl groups, which may contain from one to four nitrogen atoms and/or a phosphorus atom, are pyridine, phosphabenzene, pyridazine, pyrimidine, pyrazine, 1,3,5-triazine, 1,2,4-triazine and 1,2,3-triazine. The 5-membered ring and 6-membered ring heterocycles may also be substituted by $C_1$-$C_{10}$-alkyl, $C_6$-$C_{10}$-aryl, alkylaryl having from 1 to 10 carbon atoms in the alkyl part and 6-10 carbon atoms in the aryl part, trialkylsilyl or halogens such as fluorine, chlorine or bromine or be fused with one or more aromatics or heteroaromatics. Examples of benzo-fused 5-membered heteroaryl groups are indole, indazole, benzofuran, benzothiophene, benzothiazole, benzoxazole and benzimidazole. Examples of benzo-fused 6-membered heteroaryl groups are chromane, benzopyran, quinoline, isoquinoline, cinnoline, phthalazine, quinazoline, quinoxaline, 1,10-phenanthroline and quinolizine. Nomenclature and numbering of the heterocycles has been taken from Lettau, Chemie der Heterocyclen, 1st edition, VEB, Weinheim 1979. The heterocycles are fused to the basic cyclopentadienyl skeleton via a C—C double bond of the heterocycle. Heterocycles containing one heteroatom are preferably 2,3- or b-fused.

Variation of the substituents $R^{1A}$-$R^{5A}$ which do not form the heterocycle likewise enables the polymerization behavior and the solubility of the monocyclopentadienyl complexes of the present invention to be influenced. The number and type of substituents allows the access of the olefins to be polymerized to the metal atom M to be influenced. In this way, the activity and selectivity of the catalyst in respect of various monomers, in particular bulky monomers, can be modified. Since the substituents can also influence the rate of termination reactions of the growing polymer chain, they also allow the molecular weight of the polymers formed to be altered. The chemical structure of the substituents $R^{1A}$ to $R^{5A}$ can therefore be varied within a wide range in order to achieve the desired results and obtain a tailored catalyst system. Examples of possible carboorganic substituents $R^{1A}$-$R^{5A}$ are: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropane, cyclobutane, cyclopentane, cyclohexane, cycloheptane, cyclooctane, cyclononane or cyclododecane, $C_2$-$C_{20}$-alkenyl which may be linear, cyclic or branched and can have an internal or terminal double bond, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups as substituents, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, or arylalkyl which may bear further alkyl groups as substituents, e.g. benzyl, o-, m-, p-methylbenzyl, 1- or 2-ethylphenyl, where two $R^{1A}$ to $R^{5A}$ may also be joined to form a 5- or 6-membered ring and the organic radicals $R^{1A}$-$R^{5A}$ may also be substituted by halogens, e.g. fluorine, chlorine or bromine. Possible organosilicon substituents $SiR^{6A}_3$ can bear radicals $R^{6A}$ which are the same as those described above for $R^{1A}$-$R^{5A}$, where two $R^{6A}$ may also be joined to form a 5- or 6-membered ring, e.g. trimethylsilyl, triethylsilyl, butyldimethylsilyl, tributylsilyl, triallylsilyl, triphenylsilyl or dimethylphenylsilyl. Preferred radicals $R^{1A}$-$R^{5A}$ are hydrogen, methyl, ethyl, n-propyl, isopropyl, n-butyl, isobutyl, tert-butyl, n-pentyl, n-hexyl, n-heptyl, n-octyl, vinyl, allyl, benzyl, phenyl, ortho-dialkyl- or ortho-dichloro-substituted phenyls, trialkyl- or trichloro-substituted phenyls, naphthyl, biphenyl and anthranyl. Particularly useful organosilicon substituents are trialkylsilyl groups having from 1 to 10 carbon atoms in the alkyl radical, in particular trimethylsilyl groups. Preference is also given to compounds in which two vicinal radicals $R^{1A}$-$R^{5A}$ form a fused ring system, i.e. together with the $E^{1A}$-$E^{5A}$ skeleton, preferably $C_5$-cyclopentadienyl skeleton, form, for example, an unsubstituted or substituted indenyl, benzindenyl or tetrahydroindenyl system.

Examples of cyclopentadienyl systems HCp containing a fused heterocycle are thiapentalene, 2-methylthiapentalene, 2-ethylthiapentalene, 2-isopropylthiapentalene, 2-n-butylthiapentalene, 2-tert-butylthiapentalene, 2-trimethylsilylthiapentalene, 2-phenylthiapentalene, 2-naphthylthiapentalene, 3-methylthiopentalene, 4-phenyl-2,6-dimethyl-1-thiopentalene, 4-phenyl-2,6-diethyl-1-thiopentalene, 4-phenyl-2,6-diisopropyl-1-thiopentalene, 4-phenyl-2,6-di-n-butyl-1-thiopentalene, 4-phenyl-2,6-di-trimethylsilyl-1-thiopentalene, azapentalene, 2-methylazapentalene, 2-ethylazapentalene, 2-isopropylazapentalene, 2-n-butylazapentalene, 2-trimethylsilylazapentalene, 2-phenylazapentalene, 2-naphthylazapentalene, 1-phenyl-2,5-dimethyl-1-azapentalene, 1-phenyl-2,5-diethyl-1-azapentalene, 1-phenyl-2,5-di-n-butyl-1-azapentalene, 1-phenyl-2,5-di-tert-butyl-1-azapentalene, 1-phenyl-2,5-di-trimethylsilyl-1-azapentalene, 1-tert-butyl-2,5-dimethyl-1-azapentalene, oxapentalene, phosphapentalene, 1-phenyl-2,5-dimethyl-1-phosphapentalene, 1-phenyl-2,5-diethyl-1-phosphapentalene, 1-phenyl-2,5-di-n-butyl-1-phosphapentalene, 1-phenyl-2,5-di-tert-butyl-1-phosphapentalene, 1-phenyl-2,5-di-trimethylsilyl-1-phosphapentalene, 1-methyl-2,5-dimethyl-1-phosphapentalene, 1-tert-butyl-2,5-dimethyl-1-phosphapentalene, 7-cyclopenta[1,2]thiophene[3,4]-cyclopentadienes or 7-cyclopenta[1,2]pyrrole[3,4]-cyclopentadienes.

In further preferred cyclopentadienyl systems HCp, four of the radicals $R^{1A}$-$R^{5A}$, i.e. two pairs of vicinal radicals, form two heterocycles. The heterocyclic systems are as described in more detail above. Examples of cyclopentadienyl systems HCp containing two fused heterocycles are 7-cyclopentadithiophene, 7-cyclopentadipyrrole or 7-cyclopentadiphosphole.

The synthesis of such cyclopentadienyl systems HCp is described, for example, in the abovementioned WO 98/22486. In "metalorganic catalysts for synthesis and polymerisation", Springer Verlag 1999, Ewen et al. describe, on pages 150 ff., further syntheses of cyclopentadienyl systems HCp.

As in the case of metallocenes, the monocyclopentadienyl complexes of the present invention can be chiral. Thus, one of the substituents $R^{1A}$-$R^{5A}$ of the basic cyclopentadienyl skeleton can have one or more chiral centers, or the cyclopentadienyl system HCp can itself be enantiotopic so that chirality is induced only when it is bound to the transition metal M (for the formalisms employed for the chirality of cyclopentadienyl compounds, see R. Halterman, Chem. Rev. 92, (1992), 965-994).

Y is a substituent which is bound to HCp and comprises at least one uncharged donor which contains an atom of group 15 or 16 of the Periodic Table. The substituent Y can be bound to the basic cyclopentadienyl skeleton or to the heterocycle. Y is preferably bound to the basic cyclopentadienyl skeleton and replaces a substituent $R^{1A}$-$R^{5A}$. Y is very particularly preferably bound to the cyclopentadienyl skeleton in a position next to the fused-on heterocycle. Thus, if the heterocycle is fused on in the 2,3 position of the cyclopentadiene skeleton, then Y is preferably located in the 1 or 4 position of the cyclopentadiene skeleton. The donor in Y can be bound intermolecularly or intramolecularly to the metal M. The donor in Y is preferably bound intramolecularly to M. The donor can be an uncharged functional group containing an element of group 15 or 16 of the Periodic Table, e.g. amine, imine, carboxamide, carboxylic ester, ketone (oxo), ether, thioketone, phosphine, phosphite, phosphine oxide, sulfonyl, sulfonamide or an unsubstituted, substituted or fused, heterocyclic ring system. The binding of Y to the donor can be carried out, for example, by methods analogous to those described by M. Enders et al. in Chem. Ber. (1996), 129, 459-463 or P. Jutzi and U. Siemeling in J. Orgmet. Chem. (1995), 500, 175-185.

M is a metal of group 3, 4, 5, 6, 7, 8, 9 or 10 of the Periodic Table, preferably of group 3, 4, 5 or 6 of the Periodic Table, for example scandium, yttrium, titanium, zirconium, hafnium, vanadium, molybdenum, tantalum, chromium or tungsten. M is very particularly preferably titanium or chromium. The metal complexes, in particular the chromium complexes, can be obtained in a simple manner by reacting the corresponding metal salts, e.g. metal chlorides, with the ligand anion (e.g. by a procedure analogous to the examples in DE 187 10615).

Among the monocyclopentadienyl complexes of the present invention, preference is given to ones of the formula (HCp)YMX$_k$, where the variables have the following meanings:

HCp is a cyclopentadienyl system containing at least one fused heterocycle,

Y is a substituent which is bound to HCp and comprises at least one uncharged donor containing an atom of group 14 or 15 of the Periodic Table, M is a metal of group 3, 4, 5 or 6 of the Periodic Table, X are each, independently of one another, fluorine, chlorine, bromine, iodine, hydrogen, $C_1$-$C_{10}$-alkyl, $C_2$-$C_{10}$-alkenyl, $C_6$-$C_{20}$-aryl, alkylaryl having 1-10 carbon atoms in the alkyl part and 6-20 carbon atoms in the aryl part, $NR^1R^2$, $OR^1$, $SR^1$, $SO_3R^1$, $OC(O)R^1$, CN, SCN, β-diketonate, CO, $BF_4^-$, $PF_6^-$ or bulky noncoordinating anions, $R^1$-$R^2$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $SiR^3_3$, where the organic radicals $R^1$-$R^2$ may also be substituted by halogens and two radicals $R^1$-$R^2$ may also be joined to form a five- or six-membered ring, $R^3$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two radicals $R^3$ may also be joined to form a five- or six-membered ring, and k is 1, 2 or 3.

The above-described embodiments and preferred embodiments for HCp and Y also apply to these preferred monocyclopentadienyl complexes.

M is a metal of group 3, 4, 5 or 6 of the Periodic Table, preferably group 4, 5 or 6 of the Periodic Table, for example titanium, zirconium, hafnium, vanadium, molybdenum, tantalum, chromium or tungsten. Very particular preference is given to M being titanium in the oxidation state 3 or chromium, in particular in the oxidation state 3 or 4.

The ligands X are determined, for example, by the choice of the corresponding starting metal compounds used for the synthesis of the monocyclopentadienyl complexes, but can also be changed subsequently. Possible ligands X are, in particular, the halogens fluorine, chlorine, bromine or iodine, in particular chlorine. Alkyl radicals such as methyl, ethyl, propyl, butyl, vinyl, allyl, phenyl and benzyl are also advantageous ligands X. Further ligands X which may be mentioned by way of example and do not constitute an exhaustive listing are trifluoroacetate, $BF_4^-$, $PF_6^-$ and also weakly coordinating or noncoordinating anions (cf., for example, S. Strauss in Chem. Rev. 1993, 93, 927-942), for example $B(C_6F_5)_4^-$.

Amides, alkoxides, sulfonates, carboxylates and β-diketonates are particularly useful ligands X. Varying the radicals $R^1$ and $R^2$ enables, for example, fine adjustments to be made to physical properties such as solubility. Examples of possible carboorganic substituents $R^1$-$R^2$ are the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropane, cyclobutane, cyclopentane, cyclohexane, cycloheptane, cyclooctane, cyclononane or cyclododecane, $C_2$-$C_{20}$-alkenyl which may be linear, cyclic or branched and have an internal or terminal double bond, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups as substituents, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, or arylalkyl which may bear further alkyl groups as substituents, e.g. benzyl, o-, m-, p-methylbenzyl, 1- or 2-ethylphenyl, where $R^1$ may also be joined to $R^2$ to form a 5- or 6-membered ring and the organic radicals $R^1$-$R^2$ may also be substituted by halogens such as fluorine, chlorine or bromine. Possible radicals $R^3$ in an organosilicon substituent $SiR^3_3$ can be the same radicals as described in more detail above for $R^1$-$R^2$, where two $R^3$ may also be joined to form a 5- or 6-membered ring, e.g. trimethylsilyl, triethylsilyl, butyldimethylsilyl, tributylsilyl, triallylsilyl, triphenylsilyl or dimethylphenylsilyl. Preference is given to using $C_1$-$C_{10}$-alkyl such as methyl, ethyl, n-propyl, n-butyl, tert-butyl, n-pentyl, n-hexyl, n-heptyl, n-octyl, and also vinyl, allyl, benzyl and phenyl as radicals $R^1$ and $R^2$. Very particular preference is given to using some of the substituted ligands X since they can be obtained from cheap and readily available starting materials. Thus, a particularly preferred embodiment is obtained when X is dimethylamide, methoxide, ethoxide, isopropoxide, phenoxide, naphthoxide, triflate, p-toluenesulfonate, acetate or acetylacetonate.

The number k of the ligands X depends on the oxidation state of the transition metal M. The number k can therefore not be given as a generally applicable figure. The oxidation states of the transition metals M in catalytically active complexes are mostly known to those skilled in the art. Chromium, molybdenum and tungsten are very probably present in the oxidation state +3. However, it is also possible to use complexes whose oxidation state does not correspond to that of the active catalyst. Such complexes can then be appropriately reduced or oxidized by means of suitable activators. Preference is given to using chromium complexes in the oxidation state +3 or +4 and titanium complexes in the oxidation state +3 or +4.

In preferred monocyclopentadienyl complexes, the cyclopentadienyl system HCp and Y form a ligand (HCp-Y) of the formula II:

(II)

where the variables Y, $E^{1A}$ to $E^{5A}$ and $R^{6A}$ are as defined above and their preferred embodiments are also preferred here and $R^{1A}$-$R^{4A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $SiR^{6A}_3$, where the organic radicals $R^{1A}$-$R^{4A}$ may also be substituted by halogens and two vicinal radicals $R^{1A}$-$R^{4A}$ may also be joined to form a five- or six-membered ring, with the proviso that at least two vicinal radicals $R^{1A}$-$R^{4A}$ are joined to form a heterocycle which contains at least one atom from group 15 or 16 of the Periodic Table.

The embodiments and preferred embodiments described above likewise apply to $R^{1A}$-$R^{4A}$.

In particularly preferred monocyclopentadienyl complexes, Y is a substituent of the formula -$Z_m$-A, where the variables have the following meanings:

Z is a divalent bridge between A and HCp,

A is $NR^4R^5$, $PR^4R^5$, $OR^4$, $SR^4$ or an unsubstituted, substituted or fused, heterocyclic ring system, $R^4$-$R^5$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $SiR^6_3$, where the organic radicals $R^4$ and $R^5$ may also be substituted by halogen and two radicals $R^4$ and $R^5$ may also be joined to form a five- or six-membered ring, $R^6$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, and two radicals $R^6$ may also be joined to form a five- or six-membered ring, and m is 1, or may also be 0 when A is an unsubstituted, substituted or fused, heteroaromatic ring system.

A may, for example together with bridge Z, form an amine, ether, thioether or phosphine. A can, however, also be an unsubstituted, substituted or fused, heterocyclic, preferably heteroaromatic, ring system which can contain heteroatoms selected from the group consisting of oxygen, sulfur, nitrogen and phosphorus in addition to the carbon ring members. Examples of 5-membered ring heteroaryl groups which contain from one to four nitrogen atoms or from one to three nitrogen atoms and/or a sulfur or oxygen atom as ring members in addition to carbon atoms are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4'-oxadiazol-2-yl or 1,2,4-triazol-3-yl. Examples of 6-membered heteroaryl groups which can contain from one to four nitrogen atoms and/or a phosphorus atom are 2-pyridinyl, 2-phosphabenzoyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl or 1,2,4-triazin-6-yl. The 5- and 6-membered ring heteroaryl groups may also be substituted by $C_1$-$C_{10}$-alkyl, $C_6$-$C_{10}$-aryl, alkylaryl having from 1 to 10 carbon atoms in the alkyl part and 6-10 carbon atoms in the aryl part, trialkylsilyl or halogens such as fluorine, chlorine, bromine or be fused with one or more aromatics or heteroaromatics. Examples of benzofused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl and 7-benzimidazolyl. Examples of benzo-fused 6-membered heteroaryl groups are 2-quinolyl, 8-quinolyl, 3-cinnolyl, 8-cinnolyl, 1-phthalazlyl, 2-quinazolyl, 4-quinazolyl, 8-quinazolyl, 5-quinoxalyl, 4-acridyl, 1-phenanthridyl and 1-phenazyl. Among these heteroaromatic systems, particular preference is given to substituted and unsubstituted 2-pyridyl and 8-quinolyl.

Appropriate choice of the radicals $R^4$ to $R^5$ likewise enables an influence to be exerted on the activity of the catalyst and on the molecular weight of the polymer formed. Possible substituents $R^4$ to $R^5$ are the same radicals described for $R^1$-$R^2$, where two vicinal radicals $R^4$ and $R^5$ may also be joined to form a 5- or 6-membered ring and may be substituted by halogens such as fluorine, chlorine or bromine. Preferred radicals $R^4$ and $R^5$ are hydrogen, methyl, ethyl, n-propyl, isopropyl, n-butyl, tert-butyl, n-pentyl, n-hexyl, n-heptyl, n-octyl, vinyl, allyl, benzyl, phenyl, naphthyl, biphenyl and anthranyl. Preference is likewise given to structures in which $R^4$ and $R^5$ together with the heteroatom bearing them form a heterocycle such as pyrrolidine or piperidine. Possible organosilicon substituents are, in particular, trialkylsilyl groups having from 1 to 10 carbon atoms in the alkyl radical, in particular trimethylsilyl groups.

The bridge Z between the cyclopentadienyl system HCp and the functional group A is an organic diradical comprising carbon and/or silicon units and having a chain length of from 1 to 5. Z can be bound to the basic cyclopentadienyl skeleton or to the heterocycle. Z is preferably bound to the cyclopentadienyl skeleton. Changing the length of the linkage between the cyclopentadienyl system and the heteroatom donor A enables the activity of the catalyst to be influenced. Preferred Z are

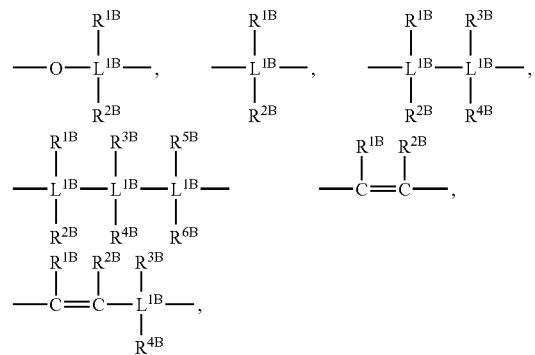

=$BR^{1B}$, =$BNR^{1B}R^{2B}$, =$AlR^{1B}$, —Ge—, —Sn—, —O—, —S—, =SO, =$SO_2$, =$NR^{1B}$=CO, =$PR^{1B}$ or =$P(O)R^{1B}$, where $R^{1B}$-$R^{6B}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $SiR^{7B}_3$, where the organic radicals $R^{1B}$-$R^{6B}$ may also be substituted by halogens and two radicals $R^{1B}$-$R^{6B}$ may also be joined to form a five- or six-membered ring, $R^{7B}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two radicals $R^{7B}$ may also be joined to form a five- or six-membered ring, and $L^{1B}$ is carbon, silicon or germanium, preferably carbon or silicon.

Possible substituents $R^{1B}$ to $R^{6B}$ are the same radicals as described for $R^1$-$R^2$, where two geminal or vicinal radicals $R^{1B}$ to $R^{6B}$ may also be joined to form a 5- or 6-membered ring and may also be substituted by halogens such as fluorine, chlorine or bromine. Preferred radicals $R^{1B}$ to $R^{6B}$ are hydrogen, methyl, ethyl, n-propyl, isopropyl, n-butyl, tert-butyl, n-pentyl, n-hexyl, n-heptyl, n-octyl, vinyl, allyl, benzyl, phenyl, naphthyl, biphenyl and anthranyl. Possible organosilicon substituents are, in particular, trialkylsilyl groups having from 1 to 10 carbon atoms in the alkyl radical, especially trimethylsilyl groups.

In preferred monocyclopentadienyl complexes, the cyclopentadienyl system HCp and -Z-A form a ligand (CP-Z-A) of the formula III:

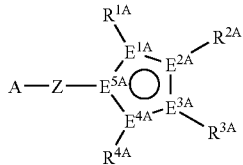
(III)

where the variables A, Z, $E^{1A}$ to $E^{5A}$ and $R^{6A}$ are as defined above and their preferred embodiments are also preferred here and $R^{1A}$-$R^{4A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $SiR^{6A}{}_3$, where the organic radicals $R^{1A}$-$R^{4A}$ may also be substituted by halogens and two vicinal radicals $R^{1A}$-$R^{4A}$ may also be joined to form a five- or six-membered ring, with the proviso that at least two vicinal radicals $R^{1A}$-$R^{4A}$ are joined to form a heterocycle which contains at least one atom from group 15 or 16 of the Periodic Table.

The embodiments and preferred embodiments described above likewise apply to $R^{1A}$-$R^{4A}$.

Among these monocyclopentadienyl complexes, particular preference is given to ones in which m is 1 and A is $NR^4R^5$, $PR^4R^5$, $OR^4$ or $SR^4$, preferably is $NR^4R^5$ or $PR^4R^5$ and Z is a divalent bridge selected from the group consisting of

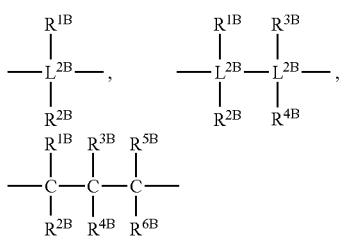

where $L^{2B}$ are each, independently of one another, carbon or silicon, $R^{1B}$-$R^{6B}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{7B}{}_3$, where the organic radicals $R^{1B}$-$R^{6B}$ may also be substituted by halogens and two geminal or vicinal radicals $R^{1B}$-$R^{6B}$ may also be joined to form a five- or six-membered ring and $R^{7B}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{7B}$ may also be joined to form a five- or six-membered ring.

The abovementioned embodiments and preferred embodiments for $R^{1B}$-$R^{7B}$ also apply to these preferred monocyclopentadienyl complexes. Owing to the ease with which they can be prepared, preference is given to the combination of Z=$CH_2$, $SiMe_2$, CH=CH or 1,2-phenylene with A=$NR^4R^5$ or $PR^4R^5$.

A further preferred embodiment is a monocyclopentadienyl complex in which

A is an unsubstituted, substituted or fused, heteroaromatic ring system and

Z is

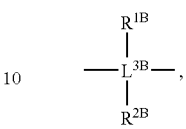

where $L^{3B}$ are each, independently of one another, carbon or silicon, $R^{1B}$-$R^{2B}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl radical and 6-20 carbon atoms in the aryl radical or $SiR^{7B}{}_3$, where the organic radicals $R^{1B}$-$R^{2B}$ may also be substituted by halogens and two radicals $R^{1B}$-$R^{2B}$ may also be joined to form a five- or six-membered ring and $R^{7B}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl radical and 6-20 carbon atoms in the aryl radical and two radicals $R^{7B}$ may also be joined to form a five- or six-membered ring, and m is 0 or 1.

The above-described embodiments and preferred embodiments for $R^{1B}$-$R^{2B}$ and $R^{7B}$ also apply to these preferred monocyclopentadienyl complexes.

In these preferred embodiments, A is an unsubstituted, substituted or fused, heteroaromatic ring system. Preference is given to simple systems which are readily available and cheap and are selected from the following group:

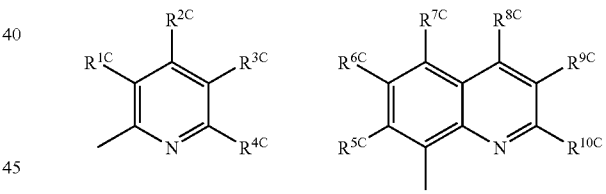

2-pyridyl    8-quinolyl $R^{1C}$-$R^{10C}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{11C}{}_3$, where the organic radicals $R^{1C}$-$R^{10C}$ may also be substituted by halogens and two vicinal radicals $R^{1C}$-$R^{10C}$ may also be joined to form a five- or six-membered ring and $R^{11C}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{11C}$ may also be joined to form a five- or six-membered ring.

Possible substituents $R^{1C}$ to $R^{10C}$ are the same radicals as described for $R^1$-$R^2$, where two vicinal radicals $R^{1C}$ to $R^{10C}$ may also be joined to form a 5- or 6-membered ring and may also be substituted by halogens such as fluorine, chlorine or bromine. Preferred radicals $R^{1C}$ to $R^{10C}$ are hydrogen, methyl, ethyl, n-propyl, isopropyl, n-butyl, tert-butyl, n-pentyl, n-hexyl, n-heptyl, n-octyl, benzyl, phenyl, naphthyl, biphenyl and anthranyl. Particularly useful organosilicon substituents are trialkylsilyl groups having from 1 to 10 carbon atoms in the alkyl radical, in particular trimethylsilyl groups.

A preferred combination of Z and A is given by A being an unsubstituted or substituted 2-pyridyl, m being 1 and Z being $CH_2$, $CMe_2$ or $SiMe_2$.

Monocyclopentadienyl complexes which are very particularly readily available and thus preferred also include ones without a bridge Z in which m is 0 and A is an unsubstituted or substituted 8-quinolyl. In these complexes, $R^{5C}$ to $R^{10C}$ is preferably hydrogen, or $R^{5C}$ to $R^{9C}$ are each hydrogen and $R^{10C}$ is methyl, ethyl, n-propyl, n-butyl, tert-butyl, n-pentyl, n-hexyl, n-heptyl, n-octyl, benzyl, phenyl, naphthyl, biphenyl or anthranyl. These are simple to prepare and at the same time display very high activities.

The monocyclopentadienyl complexes of the present invention can be used either alone or together with further components as catalyst systems for olefin polymerization. Furthermore, we have found a catalyst system for olefin polymerization comprising A) at least one monocyclopentadienyl complex according to the present invention,
B) optionally an organic or inorganic support,
C) optionally one or more cation-forming compounds,
D) optionally one or more catalysts suitable for olefin polymerization and
E) optionally one or more metal compounds of group 1, 2 or 13 of the Periodic Table.

Thus, more than one of the monocyclopentadienyl complexes of the present invention can simultaneously be brought into contact with the olefin or olefins to be polymerized. This has the advantage that it enables a wide range of polymers to be produced. For example, bimodal products can be prepared in this way.

To enable the monocyclopentadienyl complexes of the present invention to be used in polymerization processes in the gas phase or in suspension, it is often advantageous for the metallocenes to be used in the form of a solid, i.e. for them to be applied to a solid support B). Furthermore, the supported monocyclopentadienyl complexes display a high productivity. The monocyclopentadienyl complexes of the present invention can therefore also optionally be immobilized on an organic or inorganic support B) and be used in supported form in the polymerization. This is a customary method of avoiding deposits in the reactor and of controlling the polymer morphology. As support materials, preference is given to using silica gel, magnesium chloride, aluminum oxide, mesoporous materials, aluminosilicates, hydrotalcites and organic polymers such as polyethylene, polypropylene or polystyrene.

As solid support materials B) for catalysts for olefin polymerization, preference is given to using silica gels since particles whose size and structure make them suitable as supports for olefin polymerization can be produced from this material. Spray-dried silica gels, which are spherical agglomerates of smaller granular particles, known as primary particles, have been found to be particularly useful. The silica gels can be dried and/or calcined before use.

Likewise preferred supports B) are hydrotalcites and calcined hydrotalcites. In mineralogy, hydrotalcite is a natural mineral which has the ideal formula

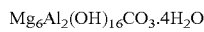

and whose structure is derived from that of brucite $Mg(OH)_2$. Brucite crystallizes in a layer structure in which the metal ions are located in octahedral holes between two layers of close-packed hydroxyl ions, with only every second layer of the octahedral holes being occupied. In hydrotalcite, some magnesium ions are replaced by aluminum ions, with the set of layers acquiring a positive charge. This is compensated by anions which together with waiter of crystallization are located in the intermediate layers.

Such layer structures are found not only in the case of magnesium-aluminum hydroxides, but generally in mixed metal hydroxides having a layer structure and the formula

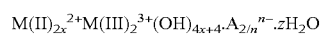

where M(II) is a divalent metal such as Mg, Zn, Cu, Ni, Co, Mn, Ca and/or Fe and M(III) is a trivalent metal such as Al, Fe, Co, Mn, La, Ce and/or Cr, x is a number from 0.5 to 10 in steps of 0.5, A is an interstitial anion and n is the charge on the interstitial anion, which may be from 1 to 8, usually from 1 to 4, and z is an integer from 1 to 6, in particular from 2 to 4. Possible interstitial anions are organic anions such as alkoxide anions, alkyl ether sulfates, aryl ether sulfates or glycol ether sulfates, inorganic anions such as, in particular, carbonate, hydrogencarbonate, nitrate, chloride, sulfate or $B(OH)_4^-$ or polyoxo metal anions such as $Mo_7O_{24}^{6-}$ or $V_{10}O_{28}^{6-}$. However, a mixture of a plurality of such anions may also be present.

Accordingly, all such mixed metal hydroxides having a layer structure are regarded as hydrotalcites for the purposes of the present invention.

Hydrotalcites can be converted by calcination, i.e. heating, into calcined hydrotalcites, which enables, inter alia, the desired hydroxyl group content to be set. In addition, the crystal structure also changes. The preparation of the calcined hydrotalcites used according to the present invention is usually carried out at above 180° C. Preference is given to calcination for from 3 to 24 hours at from 250° C. to 1000° C., in particular from 400° C. to 700° C. Simultaneously passing air or inert gas over the material being calcined or application of vacuum is also possible.

On heating, the natural or synthetic hydrotalcites firstly give off water, i.e. drying occurs. On further heating, the actual calcination process, the metal hydroxides eliminate hydroxyl groups and interstitial anions to form metal oxides, with OH groups or interstitial anions such as carbonate still being able to be present in the calcined hydrotalcites. A measure of this is the loss on ignition. This is the weight loss experienced by a sample which is heated in two steps, firstly for 30 minutes at 200° C. in a drying oven and then for 1 hour at 950° C. in a muffle furnace.

The calcined hydrotalcites used as component B) are thus mixed oxides of divalent and trivalent metals M(II) and M(III), with the molar ratio of M(II) to M(III) generally being in the range from 0.5 to 10, preferably from 0.75 to 8 and in particular from 1 to 4. Furthermore, normal levels of impurities, for example Si, Fe, Na, Ca or Ti and chlorides and sulfates, may also be present.

Preferred calcined hydrotalcites B) are mixed oxides in which M(II) is magnesium and M(III) is aluminum. Such aluminum-magnesium mixed oxides are obtainable from Condea Chemie GmbH, Hamburg, under the trade name Puralox Mg.

Preference is also given to calcined hydrotalcites in which the structural transformation is complete or virtually complete. Calcination, i.e. a transformation of the structure, can be established, for example, by means of X-ray diffraction patterns.

The hydrotalcites, calcined hydrotalcites or silica gels used are generally employed as finely divided powders having a mean particle diameter $d_{50}$ of from 5 to 200 µm, preferably from 10 to 150 µm, particularly preferably from 15 to 100 µm, and in particular from 20 to 70 µm, and usually have pore volumes of from 0.1 to 10 cm³/g, preferably from 0.2 to 5 cm³/g, and specific surface areas of from 30 to 1000 m²/g, preferably from 50 to 800 m²/g and in particular from 100 to 600 m²/g. The monocyclopentadienyl complexes of the present invention are preferably applied in such an amount that the concentration of monocyclopentadienyl complexes in the finished catalyst system is from 10 to 200 µmol, preferably from 20 to 100 µmol and particularly preferably from 25 to 70 µmol, per g of support B).

Some of the monocyclopentadienyl complexes of the present invention have only a low polymerization activity and are therefore brought into contact with an activator, viz. the component C), in order to be able to display a good polymerization activity. The catalyst system therefore optionally further comprises, as component C), one or more cation-forming compounds, preferably at least one cation-forming compound C).

Suitable cation-forming compounds C) which are able to react with the monocyclopentadienyl complex A) to convert it into a cationic compound are, for example, aluminoxanes, strong uncharged Lewis acids, ionic compounds having a Lewis-acid cation or ionic compounds having a Brönsted acid as cation.

As aluminoxanes, it is possible to use, for example, the compounds described in WO 00/31090. Particularly useful compounds are open-chain or cyclic aluminoxane compounds of the formulae (F X) or (F XI)

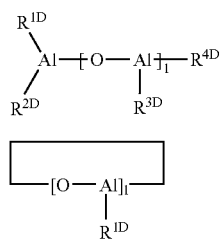

(F X)

(F XI)

where $R^{1D}$-$R^{4D}$ are each, independently of one another, a $C_1$-$C_6$-alkyl group, preferably a methyl, ethyl, butyl or isobutyl group, and l is an integer from 1 to 30, preferably from 5 to 25.

A particularly useful aluminoxane compound is methylaluminoxane.

These oligomeric aluminoxane compounds are customarily prepared by controlled reaction of a solution of trialkylaluminum with water. The oligomeric aluminoxane compounds obtained in this way are generally in the form of mixtures of both linear and cyclic chain molecules of various lengths, so that l is to be regarded as a mean. The aluminoxane compounds can also be present in admixture with other metal alkyls, usually aluminum alkyls. Aluminoxane preparations suitable as component C) are commercially available.

Furthermore, modified aluminoxanes in which some of the hydrocarbon radicals in the formulae (F X) or (F XI) are replaced by hydrogen atoms or alkoxy, aryloxy, siloxy or amide groups can be used in place of the aluminoxane compounds of the formula (F X) or (F XI) as component C).

It has been found to be advantageous to use the monocyclopentadienyl complex A) and the aluminoxane compounds in such amounts that the atomic ratio of aluminum from the aluminoxane compounds, including any aluminum alkyl still present, to the transition metal from the monocyclopentadienyl complex A) is in the range from 10:1 to 1000:1, preferably from 20:1 to 500:1 and in particular from 30:1 to 400:1.

As strong, uncharged Lewis acids, preference is given to compounds of the formula (F XII)

(F XII)

where $M^{2D}$ is an element of group 13 of the Periodic Table of the Elements, in particular B, Al or Ga, preferably B, $X^{1D}$, $X^{2D}$ and $X^{3D}$ are each hydrogen, $C_1$-$C_{10}$-alkyl, $C_6$-$C_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryls, preferably pentafluorophenyl.

Further examples of strong, uncharged Lewis acids are mentioned in WO 00/31090.

Particularly useful compounds as component C) are boranes and boroxins, e.g. trialkylborane, triaryl-borane or trimethylboroxin. Particular preference is given to using boranes which bear at least two perfluorinated aryl radicals. Particular preference is given to compounds of the formula (F XII) in which $X^{1D}$, $X^{2D}$ and $X^{3D}$ are identical, preferably tris(pentafluorophenyl)borane.

Strong uncharged Lewis acids which are suitable as cation-forming compounds C) also include the reaction products from the reaction of a boronic acid with two equivalents of a trialkylaluminum or the reaction products from the reaction of a trialkylaluminum with two equivalents of an acidic fluorinated, in particular perfluorinated, carbon compound such as pentafluorophenol or bis(pentafluorophenyl)borinic acid.

Suitable ionic compounds having Lewis-acid cations include salt-like compounds of the cation of the formula (F XIII)

(F XIII)

where $M^{3D}$ is an element of groups. 1 to 16 of the Periodic Table of the Elements, Q1 to Qz are singly negatively charged groups such as $C_1$-$C_{28}$-alkyl, $C_6$-$C_{15}$-aryl, alkylaryl, arylalkyl, haloalkyl, haloaryl each having from 6 to 20 carbon atoms in the aryl radical and from 1 to 28 carbon atoms in the alkyl radical, $C_3$-$C_{10}$-cycloalkyl which may bear $C_1$-$C_{10}$-alkyl groups as substituents, halogen, $C_1$-$C_{28}$-alkoxy, $C_6$-$C_{15}$-aryloxy, silyl or mercaptyl groups, a is an integer from 1 to 6 and z is an integer from 0 to 5, d is the difference a–z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

The salts containing noncoordinating anions can also be prepared by combining a boron or aluminum compound, e.g. an aluminum alkyl, with a second compound which can react with the boron or aluminum compound so as to link two or more boron or aluminum atoms to one another, e.g. water, and a third compound which forms an ionizing ionic compound with the boron or aluminum compound, e.g. triphenylchloromethane. In addition, a fourth compound which likewise reacts with the boron or aluminum compound, e.g. pentafluorophenol, can be added.

Ionic compounds having Brönsted acids as cations preferably likewise have noncoordinating counterions. As Brönsted acid, particular preference is given to protonated amine or aniline derivatives. Preferred cations are N,N-dimethylanilinium, N,N-dimethylcyclohexylammonium and N,N-dimethylbenzylammonium and also derivatives of the latter two.

Compounds containing anionic boron heterocycles as are described in WO 9736937 are also suitable as component C), in particular dimethylaniliniumboratabenzenes or tritylboratabenzenes.

Preferred ionic compounds C) contain borates which bear at least two perfluorinated aryl radicals. Particular preference is given to N,N-dimethylanilinium tetrakis-(pentafluorophenyl)borate and in particular N,N-dimethylcyclohexylammonium tetrakis(pentafluorophenyl)-borate, N,N-dimethylbenzylammonium tetrakis(pentafluorophenyl)borate or trityl tetrakis(pentafluorophenyl)borate.

Two or more borate anions can also be linked to one another, as in the dianion $[(C_6F_5)_2B—C_6F_4—B(C_6F_5)_2]^{2-}$, or the borate anion can be bound via a bridge comprising a suitable functional group to the support surface.

Further suitable cation-forming compounds C) are listed in WO 00/31090.

The amount of strong, uncharged Lewis acids, ionic compounds having Lewis-acid cations or ionic compounds having Brönsted acids as cations is preferably from 0.1 to 20 equivalents, more preferably from 1 to 10 equivalents, based on the monocyclopentadienyl complex A).

Further suitable cation-forming compounds C) are boron-aluminum compounds such as di[bis(pentafluorophenylboroxy)]methylalane. Boron-aluminum compounds of this type are described, for example, in WO 99/06414.

It is also possible to use mixtures of all the abovementioned cation-forming compounds C). Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane.

Preference is given to using both the monocyclopentadienyl complexes A) and the cation-forming compounds C) in a solvent, with preference being given to aromatic hydrocarbons having from 6 to 20 carbon atoms, in particular xylenes, toluene, pentane, hexane, heptane or mixtures thereof.

A likewise broad product spectrum can also be obtained by use of the monocyclopentadienyl complexes A) of the present invention in combination with at least one further catalyst D) which is suitable for the polymerization of olefins. It is therefore possible to use one or more catalysts which are suitable for olefin polymerization as optional component D) in the catalyst system. Possible catalysts D) include, in particular, classical Ziegler-Natta catalysts based on titanium and classical Phillips catalysts based on chromium oxides.

Possible components D) in principle include all compounds of transition metals of groups 3 to 12 of the Periodic Table or the lanthanides which contain organic groups and preferably form catalysts which are active in olefin polymerization after reaction with the components C) in the presence of A) and optionally B) and/or E). These are usually compounds in which a monodentate or polydentate ligand is bound to the central atom via a sigma or pi bond. Suitable ligands include both those containing cyclopentadienyl radicals and those which are free of cyclopentadienyl radicals. Chem. Rev. 2000, Vol. 100, No. 4, describes many such compounds B) which are suitable for olefin polymerization. Multinuclear cyclopentadienyl complexes are also suitable for olefin polymerization.

Further particularly well-suited components D) are those containing at least one cyclopentadienyl-type ligand, which are generally referred to as metallocene complexes. Particularly useful metallocene complexes are those of the formula (F XIV)

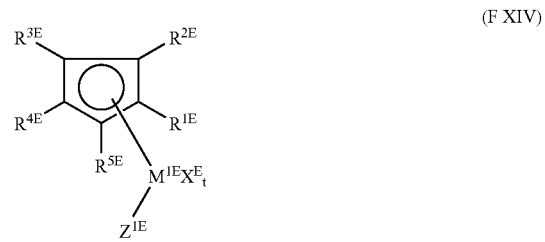

(F XIV)

where the substituents and indices have the following meanings:

$M^{1E}$ is titanium, zirconium, hafnium, vanadium, niobium, tantalum, chromium, molybdenum or tungsten, or an element of group 3 of the Periodic Table and the lanthanides, $X^E$ is fluorine, chlorine, bromine, iodine, hydrogen, $C_1$-$C_{10}$-alkyl, $C_2$-$C_{10}$-alkenyl, $C_6$-$C_{15}$-aryl, alkylaryl having from 1 to 10 carbon atoms in the alkyl part and from 6 to 20 carbon atoms in the aryl part, —$OR^{6E}$ or —$NR^{6E}R^{7E}$, or two radicals $X^E$ form a substituted or unsubstituted diene ligand, in particular a 1,3-diene ligand, and t is 1, 2 or 3 and, depending on the valence of $M^{1E}$, is such that the metallocene complex of the formula (F XIV) is uncharged, where $R^{6E}$ and $R^{7E}$ are each $C_1$-$C_{10}$-alkyl, $C_6$-$C_{15}$-aryl, alkylaryl, arylalkyl, fluoroalkyl or fluoroaryl each having from 1 to 10 carbon atoms in the alkyl radical and from 6 to 20 carbon atoms in the aryl radical and the radicals $X^E$ are identical or different and may be joined to one another, $R^{1E}$ to $R^{5E}$ are each hydrogen, $C_1$-$C_{22}$-alkyl, 5- to 7-membered cycloalkyl or cycloalkenyl which may in turn bear $C_1$-$C_{10}$-alkyl groups as substituents, $C_2$-$C_{22}$-alkenyl, $C_6$-$C_{22}$-aryl, alkylaryl or arylalkyl, where two adjacent radicals may also together form saturated or unsaturated cyclic groups having from 4 to 44 carbon atoms, or $Si(R^{8E})_3$ where $R^{8E}$ may be identical or different and may each be $C_1$-$C_{10}$-alkyl, $C_3$-$C_{10}$-cycloalkyl, $C_6$-$C_{15}$-aryl, $C_1$-$C_4$-alkoxy or $C_6$-$C_{10}$-aryloxy and $Z^{1E}$ is as defined for $X^E$ or is

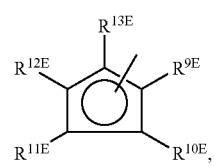

where the radicals $R^{9E}$ to $R^{13E}$ are each hydrogen, $C_1$-$C_{22}$-alkyl, 5- to 7-membered cycloalkyl or cycloalkenyl which may in turn bear $C_1$-$C_{10}$-alkyl groups as substituents, $C_2$-$C_{22}$-alkenyl, $C_6$-$C_{22}$-aryl, alkylaryl or arylalkyl, where two adjacent radicals may also together form saturated or unsaturated cyclic groups having from 4 to 44 carbon atoms, or $Si(S^{14E})_3$ where $R^{14E}$ are identical or different and are each $C_1$-$C_{10}$-alkyl, $C_3$-$C_{10}$-cycloalkyl, $C_6$-$C_{15}$-aryl, $C_1$-$C_4$-alkoxy or $C_6$-$C_{10}$-aryloxy, or the radicals $R^{4E}$ and $Z^{1E}$ together form an —$R^{15E}_v$-$A^{1E}$- group, where

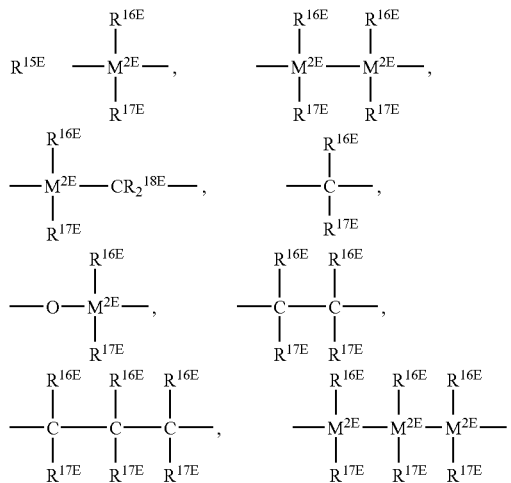

=$BR^{16E}$, =$BNR^{16E}R^{17E}$, =$AlR^{16E}$, —Ge—, —Sn—, —O— —S—, =SO, =$SO_2$, =$NR^{16E}$, =CO, =$PR^{16E}$ or =$P(O)R^{16E}$, where $R^{16E}$, $R^{17E}$ and $R^{18E}$ are identical or different and are each a hydrogen atom, a halogen atom, a trimethylsilyl group, a $C_1$-$C_{10}$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-alkoxy group, a $C_7$-$C_{15}$-alkylaryloxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group, or two adjacent radicals together with the atoms connecting them form a saturated or unsaturated ring having from 4 to 15 carbon atoms, and $M^{2E}$ is silicon, germanium or tin, preferably silicon, $A^{1E}$ is

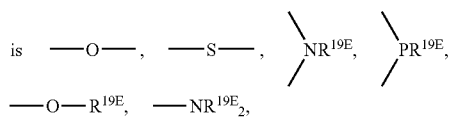

—$PR^{19E}_2$ or an unsubstituted, substituted or fused, heterocyclic ring system, where $R^{19E}$ are each, independently of one another, $C_1$-$C_{10}$-alkyl, $C_6$-$C_{15}$-aryl, $C_3$-$C_{10}$-cycloalkyl, $C_7$-$C_{18}$-alkylaryl or $Si(R^{20E})_3$, $R^{20E}$ is hydrogen, $C_1$-$C_{10}$-alkyl, $C_6$-$C_{15}$-aryl which may in turn bear $C_1$-$C_4$-alkyl groups as substituents or $C_3$-$C_{10}$-cycloalkyl, v is 1 or in the case of $A^{1E}$ being an unsubstituted, substituted or fused, heterocyclic ring system can also be 0, or the radicals $R^{4E}$ and $R^{12E}$ together form an —$R^{15E}$— group.

The radicals $X^E$ in the formula (F XIV) are preferably identical and are preferably fluorine, chlorine, bromine, $C_1$-$C_7$-alkyl or aralkyl, in particular chlorine, methyl or benzyl.

Such complexes can be synthesized by methods known per se, preferably by reaction of the appropriately substituted, cyclic hydrocarbon anions with halides of titanium, zirconium, hafnium or chromium.

Examples of particularly useful compounds D) include: bis(cyclopentadienyl)zirconium dichloride, bis(pentamethylcyclopentadienyl)zirconium dichloride, bis(methylcyclopentadienyl)zirconium dichloride, bis(ethylcyclopentadienyl)zirconium dichloride, bis(n-butylcyclopentadienyl)zirconium dichloride, bis(1-n-butyl-3-methylcyclopentadienyl)zirconium dichloride, bis(indenyl)zirconium dichloride, bis(tetrahydroindenyl)zirconium dichloride and bis(trimethylsilylcyclopentadienyl)zirconium dichloride and also the corresponding dimethylzirconium compounds.

As component D), preference is also given to bridged bis-indenyl complexes in the racemic or pseudoracemic form, where pseudoracemic refers to complexes in which the two indenyl ligands are in the racemic arrangement relative to one another when all other substituents of the complex are disregarded.

Further examples of particularly useful catalysts D) include dimethylsilanediylbis(cyclopentadienyl)zirconium dichloride, dimethylsilanediylbis(indenyl)zirconium dichloride, dimethylsilanediylbis(tetrahydroindenyl)zirconium dichloride, ethylenebis(cyclopentadienyl)zirconium dichloride, ethylenebis(indenyl)zirconium dichloride, ethylenebis(tetrahydroindenyl)zirconium dichloride, tetramethylethylene-9-fluorenylcyclopentadienylzirconium dichloride, dimethylsilanediylbis(3-tert-butyl-5-methylcyclopentadienyl)zirconium dichloride, dimethylsilanediylbis(3-tert-butyl-5-ethylcyclopentadienyl)zirconium dichloride, dimethylsilanediylbis (2-methylindenyl)zirconium dichloride, dimethyl-silanediylbis(3-methyl-5-methylcyclopentadienyl) zirconium dichloride, dimethylsilanediylbis(3-ethyl-5-isopropylcyclopentadienyl)zirconium dichloride, dimethylsilanediylbis(2-ethylindenyl)zirconium dichloride, dimethylsilanediylbis(2-methyl-4,5-benzindenyl)zirconium dichloride, dimethylsilanediylbis(2-ethyl-4,5-benzindenyl) zirconium dichloride, methylphenylsilanediylbis(2-methyl-4,5-benzindenyl)zirconium dichloride, methylphenylsilanediylbis(2-ethyl-4,5-benzindenyl)zirconium dichloride, diphenylsilanedlylbis(2-methyl-4,5-benzindenyl)zirconium dichloride, dimethylsilanediylbis(2-methyl-4-phenylindenyl)zirconium dichloride, dimethylsilanediylbis(2-ethyl-4-phenylindenyl)zirconium dichloride, dimethylsilanediylbis (2-methyl-4-(1-naphthyl)indenyl)zirconium dichloride, dimethylsilanediylbis(2-ethyl-4-(1-naphthyl)indenyl)zirconium dichloride, dimethylsilanediylbis(2-propyl-4-(1-naphthyl)indenyl)zirconium dichloride and dimethylsilanediylbis (2-i-butyl-4-(1-naphthyl)indenyl)zirconium dichloride, where these complexes are preferably used in the racemic form.

Examples of appropriate methods of preparation are described, for example, in Journal of organometallic Chemistry, 369 (1989), 359-370.

Further preferred components D) are ones in which the radicals $R^{4E}$ and $Z^{1E}$ together form an —$R^{15E}$-$A^{1E}$- group.

When $A^{1E}$ is —O—, —S—, —$NR^{19E}$— and —$PR^{19E}$—, $M^{1E}$ is preferably titanium, particularly preferably titanium in the oxidation state +4. Particularly useful complexes D) of this type are dimethylsilanediyl(tetramethylcyclopentadienyl)(benzylamino)titanium dichloride, dimethylsilanediyl(tetramethylcyclopentadienyl) (tert-butylamino) titanium dichloride, dimethylsilanediyl(tetramethylcyclopentadienyl)(adamantyl)titanium dichloride and dimethylsilanediyl(indenyl) (tert-butylamino)titanium dichloride.

When $A^{1E}$ is —O—$R^{19E}$, —$NR^{19E}_2$, —$PR^{19E}_2$ or an unsubstituted, substituted or fused, heterocyclic or heteroaromatic ring system, $M^{1E}$ is preferably titanium or chromium, where titanium is particularly preferably in the oxidation state +3 or +4 and chromium is preferably in the oxidation state +3.

In a preferred embodiment, $A^{1E}$ is an unsubstituted, substituted or fused, heteroaromatic ring system and $M^{1E}$ is chromium. Very particular preference is given to $A^{1B}$ being an unsubstituted or substituted, e.g. alkyl-substituted, quinolyl bound, in particular, in the 8 position, e.g. 8-quinolyl, 8-(2-methylquinolyl), 8-(2,3,4-trimethylquinolyl), 8-(2,3,4,5,6,7-hexamethylquinolyl, v being 0 and $M^{1E}$ being chromium. Preferred catalysts D) of this type are 1-(8-quinolyl)-2-methyl-4-methylcyclopentadienylchromium(III) dichloride, 1-(8-quinolyl)-3-isopropyl-5-methylcyclopentadienylchromium(III) dichloride, 1-(8-quinolyl)-3-tert-butyl-5-methylcyclopentadienylchromium(III) dichloride, 1-(8-quinolyl)-2,3,4,5-tetramethylcyclopentadienylchromium(III) dichloride, 1-(8-quinolyl)tetrahydroindenylchromium(III) dichloride, 1-(8-quinolyl)-indenylchromium(III) dichloride, 1-(8-quinolyl)-2-methylindenylchromium(III) dichloride, 1-(8-quinolyl)-2-isopropylindenylchromium(III) dichloride, 1-(8-quinolyl)-2-ethylindenylchromium(III) dichloride, 1-(8-quinolyl)-2-tert-butylindenylchromium(III) dichloride, 1-(8-quinolyl)benzindenylchromium(III) dichloride, 1-(8-quinolyl)-2-methylbenzindenylchromium(III) dichloride, 1-(8-(2-methylquinolyl))-2-methyl-4-methylcyclopentadienylchromium(III) dichloride, 1-(8-(2-methylquinolyl))-2,3,4,5-tetramethylcyclopentadienylchromium(III) dichloride, 1-(8-(2-methylquinolyl))tetrahydroindenylchromium(III) dichloride, 1-8-(2-methylquinolyl))indenylchromium(III) dichloride, 1-(8-(2-methylquinolyl))-2-methylindenylchromium(III) dichloride, 1-(8-(2-methylquinolyl))-2-isopropylindenylchromium(III) dichloride, 1-(8-(2-methylquinolyl))-2-ethylindenylchromium(III) dichloride, 1-(8-(2-methylquinolyl))-2-tert-butylindenylchromium(III) dichloride, 1-(8-(2-methylquinolyl))benzindenylchromium(III) dichloride or 1-(8-(2-methylquinolyl))-2-methylbenzindenylchromium(III) dichloride.

The preparation of such functional cyclopentadienyl ligands has been known for a long time. Various synthetic routes to these complexing ligands are described, for example, by M. Enders et al. in Chem. Ber. (1996), 129, 459-463 or P. Jutzi- and U. Siemeling in J. Orgmet. Chem. (1995), 500, 175-185.

The metal complexes, in particular the chromium complexes, can be obtained in a simple manner by reacting the appropriate metal salts, e.g. metal chlorides, with the ligand anion (e.g. using a procedure analogous to the examples in DE-A-19710615).

Further suitable catalysts D) include metallocenes containing at least one ligand formed by a cyclopentadienyl or heterocyclopentadienyl and a fused-on heterocycle, with the heterocycles preferably being aromatic and containing nitrogen and/or sulfur. Such compounds are described, for example, in WO 98/22486. These are, in particular, dimethylsilanediyl(2-methyl-4-phenylindenyl)(2,5-dimethyl-N-phenyl-4-azapentalene)zirconium dichloride, dimethylsilanediylbis(2-methyl-4-phenyl-4-hydroazulenyl)zirconium dichloride and dimethylsilanediylbis(2-ethyl-4-phenyl-4-hydroazulenyl)zirconium dichloride.

Suitable catalysts D) also include imidochromium compounds in which chromium bears, as structural feature, at least one imido group. These compounds and their preparation are described, for example, in WO 01/09148.

Further suitable components D) include transition metal complexes containing a tridentate macrocyclic ligand, in particular substituted and unsubstituted 1,3,5-triazacyclohexanes and 1,4,7-triazacyclononanes. In this type of catalysts, preference is likewise given to the chromium complexes. Preferred catalysts of this type are [1,3,5-trimethyl-1,3,5-triazacyclohexane]-chromium trichloride, [1,3,5-triethyl-1,3,5-triazacyclohexane]chromium trichloride, [1,3,5-trioctyl-1,3,5-triazacyclohexane]chromium trichloride, [1,3,5-tridodecyl-1,3,5-triazacyclohexane]chromium trichloride and [1,3,5-tribenzyl-1,3,5-triazacyclohexane]chromium trichloride.

Examples of further suitable catalysts D) are transition metal complexes containing at least one ligand of the formulae F XV to F XIX,

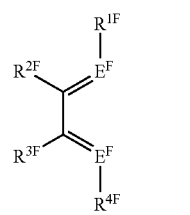

F-XV

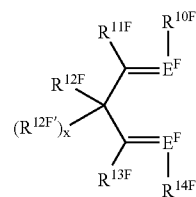

F-XVI

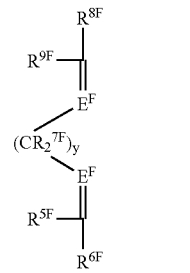

F-XVII

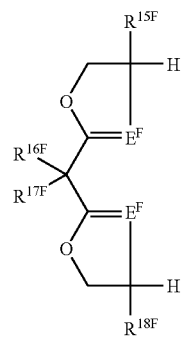

F-XVIII

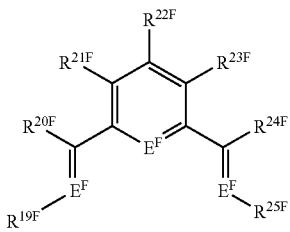

F-XIX where the transition metal is selected from among the elements Ti, Zr, Hf, Sc, V, Nb, Ta, Cr, Mo, W, Fe, Co, Ni, Pd, Pt and elements of the rare earth metals. Preference is here given to compounds having nickel, iron, cobalt or palladium as central metal.

$E^F$ is an element of group 15 of the Periodic Table of the Elements, preferably N or P, with N being particularly preferred. The two or three atoms $E^F$ in a molecule can be identical or different.

The radicals $R^{1F}$ to $R^{25F}$, which may be identical or different within a ligand system F-XV to F-XIX, are the following groups:

$R^{1F}$ and $R^{4F}$ are each, independently of one another, a hydrocarbon radical or substituted hydrocarbon radical, preferably a hydrocarbon radical in which the carbon atom adjacent to the element $E^F$ is bound to at least two carbon atoms, $R^{2F}$ and $R^{3F}$ are each, independently of one another, hydrogen, a hydrocarbon radical or a substituted hydrocarbon radical, where $R^{2F}$ and $R^{3F}$ may also together form a ring system in which one or more heteroatoms may be present, $R^{6F}$ and $R^{8F}$ are each, independently of one another, a hydrocarbon radical or substituted hydrocarbon radical, $R^{5F}$ and $R^{9F}$ are each, independently of one another, hydrogen, a hydrocarbon radical or a substituted hydrocarbon radical, where $R^{6F}$ and $R^{5F}$ or $R^{8F}$ and $R^{9F}$ may also together form a ring system, $R^{7F}$ are each, independently of one another, hydrogen, a hydrocarbon radical or a substituted hydrocarbon radical, where two $R^{7F}$ may also together form a ring system, $R^{10F}$ and $R^{14}F$ are each, independently of one another, a hydrocarbon radical or substituted hydrocarbon radical, $R^{11F}$, $R^{12F}$, $R^{12'F}$ and $R^{13F}$ are each, independently of one another, hydrogen, a hydrocarbon radical or a substituted hydrocarbon radical, where two or more geminal or vicinal radicals $R^{11A}$, $R^{12A}$, $R^{12A'}$ and $R^{13A}$ may also together form a ring system, $R^{15F}$ and $R^{18F}$ are each, independently of one another, hydrogen, a hydrocarbon radical or a substituted hydrocarbon radical, $R^{16F}$ and $R^{17}F$ are each, independently of one another, hydrogen, a hydrocarbon radical or a substituted hydrocarbon radical, $R^{19}F$ and $R^{25F}$ are each, independently of one another, $C_2$-$C_{20}$-alkenyl, $C_6$-$C_{20}$-aryl, alkylaryl having from 1 to 10 carbon atoms in the alkyl part and 6-20 carbon atoms in the aryl part, where the organic radicals $R^{19F}$ and $R^{25F}$ may also be substituted by halogens, $R^{20F}$-$R^{24F}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{26F}{}_3$, where the organic radicals $R^{20F}$—$R^{24F}$ may also be substituted by halogens and two vicinal radicals $R^{20F}$-$R^{24F}$ may also be joined to form a five- or six-membered ring and $R^{26F}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{26F}$ may also be joined to form a five- or six-membered ring, x is 0 or 1, with F-XVI being negatively charged when x is 0, and y is an integer from 1 to 4, preferably 2 or 3.

Transition metal complexes having Fe, Co, Ni, Pd or Pt as central metal and containing ligands of the formula F-XV are particularly useful. Particular preference is given to diimine complexes of Ni or Pd, e.g.:

Di(2,6-di-1-propylphenyl)-2,3-dimethyldiazabutadienepalladium dichloride, di(di-1-propylphenyl)-2,3-dimethyldiazabutadienenickel dichloride, di(2,6-di-1-propylphenyl) dimethyldiazabutadienedimethylpalladium, di(2,6-di-1-propylphenyl)-2,3-dimethyldiazabutadienedimethylnickel, di(2,6-dimethylphenyl)-2,3-dimethyldiazabutadienepalladium dichloride, di(2,6-dimethylphenyl)-2,3-dimethyldiazabutadienenickel dichloride, di(2,6-dimethylphenyl)-2,3-dimethyldiazabutadienedimethylpalladium, di(2,6-dimethylphenyl)2,3-dimethyldiazabutadienedimethylnickel, di(2-methylphenyl)-2,3-dimethyldiazabutadienepalladium dichloride, di(2-methylphenyl)-2,3-dimethyldiazabutadienenickel dichloride, di(2-methylphenyl)-2,3-dimethyldiazabutadienedimethylpalladium, di(2-methylphenyl)-2,3-dimethyldiazabutadienedimethylnickel, diphenyl-2,3-dimethyldiazabutadienepalladium dichloride, diphenyl-2,3-dimethyldiazabutadienenickel dichloride, diphenyl-2,3-dimethyldiazabutadienedimethylpalladium, diphenyl-2,3-dimethyldiazabutadienedimethylnickel, di(2,6-dimethylphenyl)azanaphthenepalladium dichloride, di(2,6-dimethylphenyl)azanaphthenenickel dichloride, di(2,6-dimethylphenyl)azanaphthenedimethylpalladium, di(2,6-dimethylphenyl)azanaphthenedimethylnickel, 1,1'-bipyridylpalladium dichloride, 1,1'-bipyridylnickel dichloride, 1,1'-bipyridyldimethylpalladium, 1,1'-bipyridyldimethylnickel.

Particularly useful compounds F-XIX also include those described in J. Am. Chem. Soc. 120, p. 4049 ff. (1998), J. Chem. Soc., Chem. Commun. 1998, 849, and Wo 98/27124. $R^{19F}$ and $R^{25F}$ in F-XIX are preferably phenyl, naphthyl, biphenyl, anthranyl, o-, m-, p-methylphenyl, 2,3-, 2,4-, 2,5- or 2,6-dimethylphenyl, -dichlorophenyl or -dibromophenyl, 2-chloro-6-methylphenyl, 2,3,4-, 2,3,5-, 2,3,6-, 2,4,5-, 2,4,6- or 3,4,5-trimethylphenyl, in particular 2,3- or 2,6-dimethylphenyl, -diisopropylphenyl, -dichlorophenyl or -dibromophenyl and 2,4,6-trimethylphenyl. At the same time, $R^{20F}$ and $R^{24F}$ are preferably hydrogen, methyl, ethyl, n-propyl, isopropyl, n-butyl, tert-butyl, n-pentyl, n-hexyl, n-heptyl, n-octyl, benzyl or phenyl, in particular hydrogen or methyl. $R^{21F}$ and $R^{23F}$ are preferably hydrogen and $R^{22F}$ is preferably hydrogen, methyl, ethyl or phenyl, in particular hydrogen. Preference is given to complexes of the ligands F-XIX with the transition metals Fe, Co or Ni, in particular Fe. Particular preference is given to 2,6-diacetylpyridinebis(2,4-dimethylphenylimine)iron dichloride, 2,6-diactylpyridinebis(2,4,6-trimethylphenylimine)iron dichloride, 2,6-diacetylpyridinebis(2-chloro-6-methylphenylimine)iron dichloride, 2,6-diacetylpyridinebis(2,6-diisopropylphenylimine)iron dichloride, 2,6-diacetylpyridinebis(2,6-dichlorophenylimine)iron dichloride, 2,6-pyridinedicarboxaldehydebis (2,6-diisopropylphenylimine)iron dichloride, 2,6-diacetylpyridinebis(2,4-dimethylphenylimine)cobalt dichloride, 2,6-diacetylpyridinebis(2,4,6-trimethylphenylimine)cobalt dichloride, 2,6-diacetylpyridinebis(2-chloro-6-methylphenylimine)cobalt dichloride, 2,6-diacetylpyridinebis(2,6-diisopropylphenylimine)cobalt dichloride, 2,6-diacetylpyridinebis(2,6-dichlorophenylimine)cobalt dichloride and 2,6-pyridinedicarboxaldehydebis(2,6-diisopropylphenylimine)cobalt dichloride.

Further catalysts D) which can be used are iminophenoxide complexes in the case of which the ligands are prepared, for example, from substituted or unsubstituted salicylaldehydes and primary amines, in particular substituted or unsubstituted arylamines. Transition metal complexes containing pi ligands containing one or more heteroatoms in the pi system, for example the boratabenzene ligand, the pyrrolyl anion or the phospholyl anion, can also be used as catalysts D).

Such combinations of components A) and D) make it possible, for example, to produce bimodal products or to generate comonomers in situ. Preference is given to using at least one monocyclopentadienyl complex A) in the presence of at least one catalyst D) which is customary for the polymerization of olefins and, if desired, one or more cation-forming compounds C). Depending on the catalyst combinations A) and D), one or more cation-forming compounds may be advantageous. The polymerization catalysts D) may likewise be supported and can be used simultaneously or in any order with the complex A) of the present invention. Mixtures of various catalysts can also be used as component D).

In addition, the catalyst system may further comprise, as additional component E), a metal compound of the formula (F-XX)

$$M^G(R^{1G})_{r^G}(R^{2G})_{s^G}(R^{3G})_{t^G} \quad (\text{F-XX})$$

where
$M^G$ is Li, Na, K, Be, Mg, Ca, Sr, Ba, boron, aluminum, gallium, indium or thallium,
$R^{1G}$ is hydrogen, $C_1$-$C_{10}$-alkyl, $C_6$-$C_{15}$-aryl, alkylaryl or arylalkyl each having from 1 to 10 carbon atoms in the alkyl part and from 6 to 20 carbon atoms in the aryl part,
$R^{2G}$ and $R^{3G}$ are each hydrogen, halogen, $C_1$-$C_{10}$-alkyl, $C_6$-$C_{15}$-aryl, alkylaryl, arylalkyl or alkoxy each having from 1 to 10 carbon atoms in the alkyl radical and from 6 to 20 carbon atoms in the aryl radical,
$r^G$ is an integer from 1 to 3 and
$s^G$ and $t^G$ are integers in the range from 0 to 2, where the sum $r^G+s^G+t^G$ corresponds to the valence of $M^G$, where the component E) is not identical to the component C). It is also possible to use mixtures of various metal compounds of the formula (F-XX).

Among the metal compounds of the formula (F-XX), preference is given to those in which
$M^G$ is lithium, magnesium or aluminum and
$R^{2G}$ and $R^{3G}$ are each $C_1$-$C_{20}$-alkyl.

Particularly preferred metal compounds of the formula (F-XX) are methyllithium, ethyllithium, n-butyllithium, methylmagnesium chloride, methylmagnesium bromide, ethylmagnesium chloride, ethylmagnesium bromide, butylmagnesium chloride, dimethylmagnesium, diethylmagnesium, dibutylmagnesium, n-butyl-n-octylmagnesium, n-butyl-n-heptylmagnesium, in particular n-butyl-n-octylmagnesium, tri-n-hexylaluminum, triisobutylaluminum, tri-n-butylaluminum, triethylaluminum, dimethylaluminum chloride, dimethylaluminum fluoride, methylaluminum dichloride, methylaluminum sesquichloride, diethylaluminum chloride and trimethylaluminum and mixtures thereof. The partial hydrolysis products of aluminum alkyls with alcohols can also be used.

When a metal compound E) is used, it is preferably present in the catalyst system in such an amount that the molar ratio of $M^G$ from formula (F-XX) to transition metal from the monocyclopentadienyl compound A) is from 2000:1 to 0.1:1, preferably from 800:1 to 0.2:1 and particularly preferably from 100:1 to 1:1.

To produce the catalyst systems of the present invention, preference is given to fixing at least one component A) together with C) to the support B) by physisorption or by chemical reaction, i.e. covalent bonding of the components to the support surface by means of reactive groups. The order in which the support component B), component A) and, if used, component C) are combined may be chosen freely. The components A) and C) can be added independently or simultaneously or in premixed form to B). After the individual process steps, the solid can be washed with suitable inert solvents such as aliphatic or aromatic hydrocarbons.

In a preferred embodiment, the monocyclopentadienyl complex A) is brought into contact with the cation-forming compound C) in a suitable solvent, usually giving a soluble reaction product, an adduct or a mixture. The preparation obtained in this way is then brought into contact with the support B), which may have been pretreated if appropriate, and the solvent is completely or partly removed. This preferably gives a solid in the form of a free-flowing powder. Examples of the industrial implementation of the above process are described in WO 96/00243, WO 98/40419 or WO 00/05277. A further preferred embodiment comprises firstly applying the cation-forming compound C) to the support B) and subsequently bringing this supported cation-forming compound into contact with the monocyclopentadienyl complex A).

The component D) can likewise be reacted in any order with the component A) and, if desired, B), C) and E). Preference is given to firstly bringing D) into contact with component C) and then proceeding as described above with the components A) and B) and possibly further C). In another preferred embodiment, a catalyst solid is prepared from the components A), B) and C) as described above and this is brought into contact with the component E) during, at the beginning of or shortly before the polymerization. Preference is given to firstly bringing E) into contact with the alpha-olefin to be polymerized and subsequently adding the catalyst solid formed from the components A), B) and C), as described above.

The monocyclopentadienyl complex A) can be brought into contact with the component(s) C) and/or D) either before or after it is brought into contact with the olefins to be polymerized. Preactivation by means of one or more components C) prior to mixing with the olefin and further addition of the same or other component(s) C) and/or D) after bringing this mixture into contact with the olefin is also possible. Preactivation is generally carried out at 10-100° C., preferably 20-80° C.

It is also possible firstly to polymerize the catalyst system with α-olefins, preferably linear $C_2$-$C_{10}$-1-alkenes and in particular ethylene or propylene, and then to use the resulting prepolymerized catalyst solid in the actual polymerization. The mass ratio of catalyst solid used in the prepolymerization to monomer polymerized onto it is usually in the range from 1:0.1 to 1:1000, preferably from 1:1 to 1:200.

Furthermore, a small amount of an olefin, preferably an α-olefin, for example vinylcyclohexane, styrene or phenyldimethylvinylsilane, as modifying component, an antistatic or a suitable inert compound such as a wax or oil can be added as additive during or after the preparation of the catalyst system. The molar ratio of additives to transition metal compound B) is usually from 1:1000 to 1000:1, preferably from 1:5 to 20:1.

The catalyst systems of the present invention are suitable for the polymerization of olefins and especially for the polymerization of α-olefins, i.e. hydrocarbons having terminal double bonds. Suitable monomers also include functionalized olefinically unsaturated compounds such as acrolein, ester or amide derivatives of acrylic or methacrylic acid, for example acrylates, methacrylates or acrylonitrile, or vinyl esters, for example vinyl acetate. Preference is given to using nonpolar olefin compounds, which include aryl-substituted α-olefins. Particularly preferred α-olefins are linear or branched $C_2$-$C_{12}$-1-alkenes, in particular linear $C_2$-$C_{10}$-1-alkenes such as ethylene, propylene, 1-butene, 1-pentene, 1-hexene, 1-heptene, 1-octene, 1-decene or branched $C_2$-$C_{10}$-1-alkenes such as 4-methyl-1-pentene, conjugated and non-conjugated dienes such as 1,3-butadiene, 1,5-hexadiene, 1,7-octadiene or vinylaromatic compounds such as styrene or substituted styrene. It is also possible to polymerize mixtures of various α-olefins. Preference is given to polymerizing at least one olefin selected from the group consisting of ethene, propene, 1-butene, 1-pentene, 1-hexene, 1-heptene, 1-octene and 1-decene.

Further suitable olefins include ones in which the double bond is part of a cyclic structure which may comprise one or more ring systems. Examples are cyclopentene, cyclohexene, norbornene or tetracyclododecene, and methylnorbornene and dienes such as 5-ethylidene-2-norbornene, norbornadiene or ethylnorbornadiene.

Mixtures of two or more olefins can also be polymerized. In contrast to some known iron and cobalt complexes, the monocyclopentadienyl complexes of the present invention display a good polymerization activity even in the case of higher α-olefins, so that their suitability for copolymerization may be particularly emphasized. In particular, the monocyclopentadienyl complexes of the present invention can be used for the polymerization or copolymerization of ethylene or propylene. As comonomers in ethylene polymerization, preference is given to using $C_3$-$C_8$-α-olefins, in particular 1-butene, 1-pentene, 1-hexene and/or 1-octene. Preference is given to using monomer mixtures containing at least 50 mol % of ethylene. Preferred comonomers in the polymerization of propylene are ethylene and/or butene.

The polymerization can be carried out in a known manner in bulk, in suspension, in the gas phase or in a supercritical medium in the customary reactors employed for the polymerization of olefins. It can be carried out batchwise or preferably continuously in one or more stages. High-pressure polymerization processes in tube reactors or autoclaves, solution processes, suspension processes, stirred gas-phase processes or gas-phase fluidized-bed processes are possible.

The polymerizations are usually carried out at from −60 to 350° C. under pressures of from 0.5 to 4000 bar at mean residence times of from 0.5 to 5 hours, preferably from 0.5 to 3 hours. The advantageous pressure and temperature ranges for carrying out the polymerization method. In high-pressure polymerization processes, which are usually carried out at pressures of from 1000 to 4000 bar, in particular from 2000 to 3500 bar, high polymerization temperatures are generally also set. Advantageous temperature ranges for these high-pressure polymerization processes are from 200 to 320° C., in particular from 220 to 290° C. In the case of low-pressure polymerization processes, it is usual to set a temperature which is at least a few degrees below the softening temperature of the polymer. In particular, temperatures of from 50 to 180° C., preferably from 70 to 120° C., are set in these polymerization processes. In the case of suspension polymerizations, polymerization is usually carried out in a suspension medium, preferably in an inert hydrocarbon such as isobutane, or else in the monomers themselves. The polymerization temperatures are generally in the range from −20 to 115° C., and the pressure is generally in the range from 1 to 100 bar. The solids content of the suspension is generally in the range from 10 to 80%. Polymerization can be carried out either batchwise, e.g. in stirring autoclaves, or continuously, e.g. in tube reactors, preferably in loop reactors. In particular, the polymerization can be carried out by the Phillips PF process, as described in U.S. Pat. No. 3,242,150 and U.S. Pat. No. 3,248,179. The gas-phase polymerization is generally carried out in the range from 30 to 125° C.

Among the polymerization processes mentioned, particular preference is given to gas-phase polymerization, in particular in gas-phase fluidized-bed reactors, solution polymerization and suspension polymerization, in particular in loop reactors and stirred tank reactors. The gas-phase polymerization can also be carried out in the condensed or supercondensed mode, in which part of the circulating gas is cooled to below the dew point and returned as a two-phase mixture to the reactor. The various polymerization processes, or else identical polymerization processes, can also, if desired, be connected in series and thus form a polymerization cascade. Furthermore, molar mass regulators, for example hydrogen, or additional additives such as antistatics can be employed in the polymerization.

The process of the present invention enables polymers of olefins to be prepared. The term polymerization as used here for describing the invention encompasses both polymerization and oligomerization, i.e. oligomers and polymers having molar masses $M_w$ in the range from about 56 to 3 000 000 can be produced by this process.

Owing to their good mechanical properties, the olefin polymers prepared using the catalyst system of the present invention are especially suitable for the production of films, fibers and moldings.

The catalyst systems of the present invention display a very high productivity in the polymerization of olefins, offer advantages in the work-up of the polymers after the polymerization and lead to significantly fewer problems in respect of catalyst residues in the polymer. The polymers prepared using the catalyst system of the present invention are advantageous for applications which require a high product purity. In addition, the catalyst systems of the present invention also display a very good activity at a relatively low molar ratio of the aluminoxane to organotransition metal compound.

EXAMPLES

Example 1

Preparation of 1-pyrrolidino-2-(2,5-dimethylthieno-[3',2':3,4]cyclopenta[1,2-b]thiophen-7-yl)ethanedichlorochromium

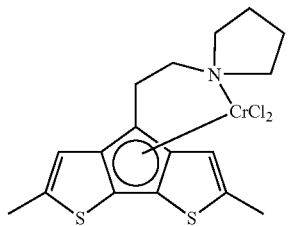

a) Preparation of the Ligand System 1-pyrrolidino-2-(2,5-dimethyl-7H-thieno[3',2':4,5]cyclopenta[b]-thiophenyl)ethane A solution of 0.95 g (4.5 mmol) of 2,5-dimethyl-7H-thieno [3',2':3,4]cyclopenta[1,2-b]thiophene in 50 ml of diethyl ether was cooled to −78° C. and admixed at this temperature with 2.8 ml (4.5 mmol) of a 1.6 M solution of n-butyllithium in hexane. The resulting suspension was allowed to warm slowly to room temperature and was subsequently stirred for another 45 minutes at room temperature. The reaction mixture was then cooled back down to −78° C. and a solution of 0.6 g (4.5 mmol) of 1-chloro-2-(1-pyrrolyl)ethane in 20 ml of diethyl ether was added dropwise at this temperature. The resulting reaction mixture was subsequently allowed to warm slowly to room temperature and was stirred for another 12 hours at room temperature.

2.8 ml of a 1.6 M solution of n-butyllithium in hexane (corresponds to 4.5 mmol of n-butyllithium) was added at room temperature to the suspension obtained in this way, which resulted in formation of a precipitate. The precipitate was separated off and washed twice with hexane. It can either be reacted directly with the chromium trichloride or can be hydrolyzed to give the ligand. For this purpose, the precipitate was admixed with 30 ml of aqueous ammonium chloride solution, 50 ml of diethyl ether were added to this mixture and the organic phase was separated off. The aqueous phase was extracted twice with 50 ml each time of diethyl ether and the organic phases were combined. The combined organic phase was washed with 50 ml of water, dried over magnesium sulfate and subsequently filtered through a short column of silica gel. Removal of the solvent and drying in a high vacuum gave 1.14 g (84% yield) of the ligand as a reddish brown oil.

NMR data for 1-pyrrolidino-2-(2,5-dimethyl-7H-thieno[3',2':4,5]cyclopenta[b]thiophenyl)ethane $^1$H-NMR (CDCl$_3$, 25° C., δ): 6.76 (q, 2H), 3.95 (t, 1H), 2.68 (m, 2H), 2.62 (m, 4H), 2.55 (s, 6H), 2.10 (q, 2H), 1.83 (m, 4H).

b) Preparation of 2-pyrrolidino-1-[2-(2,5-dimethylthieno[3',2':4,5]cyclopenta[b]thiophen-7-yl)]-ethanechromium dichloride 2.1 ml of a 1.6 M solution of n-butyllithium in hexane were added at −78° C. to a solution of 1.0 g (3.3 mmol) of 1-pyrrolidino-2-(2,5-dimethyl-7H-thieno[3',2':4,5]-cyclopenta[b]thiophen-7-yl)ethane in 50 ml of toluene. The resulting reaction mixture was subsequently allowed to warm slowly to room temperature and was stirred for another 5 hours at room temperature. The reaction mixture was then cooled back down to −78° C. and 1.3 g (3.3 mmol) of CrCl$_3$×3THF was added. The resulting reaction mixture was allowed to warm slowly to room temperature, and was stirred for another hour at room temperature and then for a further hour at 50° C. The solution was filtered to remove insoluble constituents and the solvent was removed until a volume of 10 ml remained. The concentrated solution obtained in this way was cooled to −30° C., the precipitate formed was 35' filtered off after one day, washed with cold toluene and dried. 0.61 g of the chromium complex were able to be isolated.

Example 2

Preparation of 6-(8-quinolyl)-2,5-dimethyl-3-phenyl-[cyclopenta[b]thiophenyl]chromium dichloride

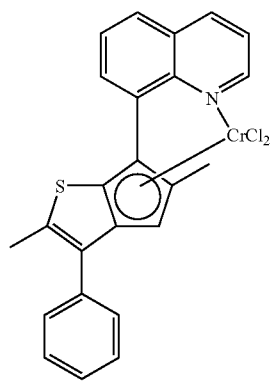

a) Preparation of the Ligand 6-(8-quinolyl)-2,5-dimethyl-3-phenyl[4-H-cyclopenta[b]thiophene]

A solution of 1.16 g of 8-bromoquinoline (5.6 mmol) in 15 ml of THF was cooled to −80° C. and admixed with 3.5 ml of a 1.6 M solution of n-butyllithium in hexane (5.6 mmol). The resulting reaction mixture was subsequently stirred at −80° C. for another 20 minutes, and a solution of 1.35 g of 4,5-dihydro-2,5-dimethyl-2-phenyl(cyclopenta[b]thiophen-6-one) (5.6 mmol) in 5 ml of THF was then added. The resulting reaction mixture was allowed to warm slowly to room temperature and was stirred for another 10 hours at room temperature. The mixture obtained in this way was poured into ice water, the aqueous phase was extracted with 30 ml of methylene chloride, dried over magnesium sulfate and the solvent was subsequently removed. This gave 1.1 g of a brown oil (an alcohol). The oil was admixed with 0.3 g of iodine and 50 ml of benzene and the mixture obtained in this way was refluxed for 0.5 hours. After cooling to room temperature, the mixture was washed with sodium carbonate solution, dried over magnesium sulfate and the solvent was removed. The product was purified by column chromatography using a 1/1 mixture of toluene/ethyl acetate as eluant and silica gel as stationary phase. This gave 0.96 g of the ligand (48% yield based on 8-bromoquinoline).

$^1$H-NMR (CDCl$_3$) of the ligand: 9.03 (m, 1H); 8.26 (m, 1H); 7.98 (m, 1H); 7.81 (m, 1H); 7.65 (m, 1H); 7.50-7.30 (m, 6H); 3.48 (s, 2H); 2.50 (s, 3H); 2.17 (s, 3H).

b) Preparation of 6-(8-quinolyl)-2,5-dimethyl-3-phenyl[cyclopenta[b]thiophenyl]chromium dichloride 1.4 ml of a 1.6 M solution of methyllithium in diethyl ether were added at −30° C. to a solution of 0.73 g (2.1 mmol) of 6-(8-quinolyl)-2,5-dimethyl-3-phenyl[4-H-cyclopenta[b]thiophene] in 20 ml of diethyl ether. The resulting reaction mixture was subsequently allowed to warm slowly to room temperature and was stirred for another hour at room temperature. The reaction mixture was then cooled to −70° C. and 0.86 g (2.3 mmol) of CrCl$_3$×3THF was added. The resulting reaction mixture was allowed to warm slowly to room temperature, was stirred at room temperature for another 6 hours and 50 ml of methylene chloride were then added. The solution was filtered to remove insoluble constituents and the solvent was removed until a volume of 3 ml remained. The concentrated solution obtained in this way was cooled to −30° C., the resulting precipitate was filtered off after one day, washed with cold diethyl ether and dried. 0.22 g of the chromium complex (21%) were able to be isolated.

Example 3

Preparation of 4-(8-quinolyl)-2,5-dimethyl-1-phenyl-[cyclopenta[b]pyrrolyl]chromium dichloride

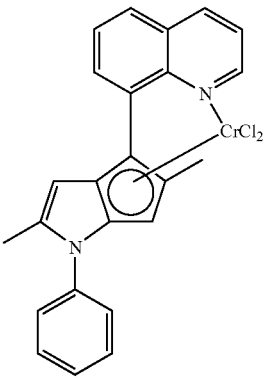

a) Preparation of the ligand system 4-(8-quinolyl)-2,5-dimethyl-7-H-1-phenyl[cyclopenta[b]pyrrole]

A solution of 10.4 g of 8-bromoquinoline (50 mmol) in 100 ml of THF was cooled to −80° C. and admixed with 20 ml of a 2.5 M solution of n-butyllithium in hexane (50 mmol). The resulting reaction mixture was subsequently stirred at −80° C. for another 15 minutes and a solution of 11.3 g of 5,6-dihydro-2,5-dimethyl-1-phenyl(cyclopenta[b]pyrrol-4-one) (50 mmol) in 30 ml of THF was then added. The resulting reaction mixture was allowed to warm slowly to room temperature and was subsequently refluxed for another 3 hours. The mixture obtained in this way was cooled to room temperature and then admixed with ice and then hydrochloric acid to bring the pH to about 1. The organic phase was separated off, the aqueous phase was admixed with ammonia solution to bring the pH to about 9, extracted with diethyl ether and the combined organic phases were dried over magnesium sulfate and the solvent was subsequently removed. The product obtained in this way was admixed with hydrochloric acid to bring the pH to 0 and the mixture was refluxed for 2 hours. Neutralization and work-up gave 10.9 g of the ligand.

b) Preparation of 4-(8-quinolyl)-2,5-dimethyl-1-phenyl[cyclopenta[b]pyrrolyl]chromium dichloride 1.0 g (3 mmol) of 4-(8-quinolyl)-2,5-dimethyl-7-H-1-phenyl[cyclopenta[b]pyrrole] was added to a solution of 0.13 g (3.1 mmol) of potassium hydride in 60 ml of THF. The resulting mixture was subsequently stirred at room temperature for another one hour and 1.12 g (3 mmol) of $CrCl_3 \times 3THF$ were then added. The resulting mixture was stirred at room temperature for another 15 hours and 50 ml of methylene chloride were then added. The solution was freed of the solvent, the residue was taken up in dichloromethane and the solution obtained in this way was filtered to remove insoluble constituents. Removal of the solvent gave 0.84 g of the chromium complex (61%).

Example 4 a) Pretreatment of the Support 100 g of ES 70×, a spray-dried silica gel from Crosfield, were heated at 130° C. for 6 hours under reduced pressure.

b) Application of the Complex to the Support 35 mg of the complex from example 1 (82.1 mmol) were admixed with 4.32 ml of a 4.75 M solution of MAO in toluene from Albemarle and the mixture was stirred for 15 minutes. The resulting solution was added over a period of 10 minutes to 2 g of the support material ES 70× from example 4a) and the mixture was stirred for another 60 minutes. The catalyst was then dried at room temperature at $10^{-3}$ mbar.

Example 5

Polymerization 400 ml of isobutane and 2 ml of a triisoprenylaluminum solution in heptane (corresponding to 75 mg of triisoprenylaluminum) were placed in a 1 l autoclave which had been made inert with argon, and 13.8 mg of the catalyst solid obtained in example 4b) were then added. Polymerization was carried out at 70° C. and an ethylene pressure of 40 bar for 60 minutes. The polymerization was stopped by releasing the pressure and the product was discharged through the bottom valve. 72 g of polyethylene were obtained.

Productivity: 520 g of PE/g of catalyst solid.

We claim:

1. A monocyclopentadienyl complex which is suitable for olefin polymerization and which comprises the following structural feature of the formula $(HCp)Y_nM$, where the variables have the following meanings:

HCp is a cyclopentadienyl system containing at least one fused heterocycle,

Y is a substitutent which is bound to HCp and comprises at least one uncharged donor containing an atom of group 14 or 15 of the Periodic Table and has the formula $-Z_m-A$, where the variables have the following meanings:

Z is a divalent bridge between A and HCp,

A is

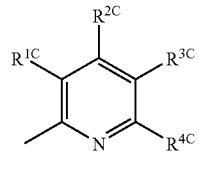
2-pyridyl

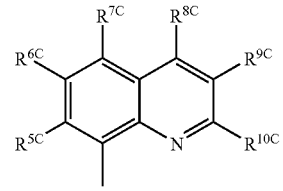
8-quinolyl where $R^{1C}$-$R^{10C}$ are each, independently of one another, hydrogen, $C_1$-$C_{20}$-alkyl, $C_2$-$C_{20}$-alkenyl, $C_6$-$C_{20}$-aryl alkylaryl having from 1 to 10 carbon atoms in the alkyl part and 6-20 carbon atoms in the aryl part or $SiR^{11C}_3$, where the organic radical $R^{1C}$-$R^{10C}$ may also be substituted by halogens and two vicinals radicals $R^{1C}$-$R^{10C}$ may also be joined to form a five- or six-membered ring and $R^{11C}$ are each independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{11C}$ may also be joined to form a five- or six-membered ring, m is 1, or may also be 0, M is a metal of group 3, 4, 5, or 6 of the Periodic Table, and n is 1, wherein HCp and Y form a ligand (HCp-Y) of the formula II

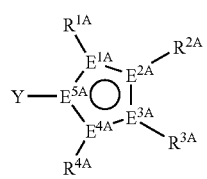

(II)

where the variables have the following meanings:

$E^{1A}$-$E^{5A}$ are each carbon or at most one $E^{1A}$ to $E^{5A}$ is phosphorus or nitrogen, $R^{1A}$-$R^{4A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $SiR^{6A}_3$, where the organic radicals $R^{1A}$-$R^{4A}$ may also be substituted by halogens and two vicinal radicals $R^{1A}$-$R^{4A}$ may also be joined to form a five- or six-membered ring, with the proviso that at least two vicinal radicals $R^{1A}$-$R^{4A}$ are joined to form a heterocycle which contains at least one atoms from group 15 or 16 of the Periodic Table.

2. The monocyclopentadienyl complex as claimed in claim 1, wherein the donor in Y is bound intramolecularly to M.

3. The monocyclopentadienyl complex as claimed in claim 1 which has the formula $(HCp)YMX_k$, where the variables have the following meanings:

X are each, independently of one another, fluorine, chlorine, bromine, iodine, hydrogen, $C_1$-$C_{10}$-alkyl, $C_2$-$C_{10}$-alkenyl, $C_6$-$C_{20}$-aryl, alkylaryl having 1-10 carbon atoms in the alkyl part and 6-20 carbon atoms in the aryl part, $NR^1R^2$, $OR^1$, $SR^1$, $SO_3R^1$, $OC(O)R^1$, CN, SCN, β-diketonate, CO, $BF_4^-$, $PF_6^-$ or bulky noncoordinating anions, $R^1$-$R^2$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $SiR^3_3$, where the organic radical $R^1$-$R^2$ may also be substituted by halogens and two radicals $R^1$-$R^2$ may also be joined to form a five- or six membered ring, $R^3$ are each, independently of one another, hydrogen, $C_1$-$C_{20}$-alkyl, $C_2$-$C_{20}$-alkenyl, alkenyl, $C_6$-$C_{20}$-aryl, alkylaryl having from 1 to 10 carbon atoms in the alkyl part and 6-20 carbon atoms in the aryl part and two radicals $R^3$ may also be joined to form a five- or six-membered ring, and k is 1, 2 or 3.

4. The monocyclopentadienyl complex as claimed in claim 1, wherein m is 1,

Z is a divalent bridge selected from the group consisting of

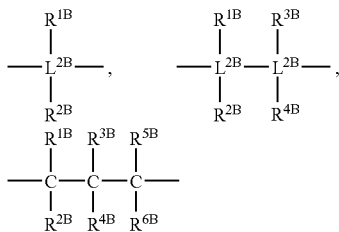

where $L^{2B}$ are each, independently of one another, carbon or silicon, $R^{1B}$-$R^{6B}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{7B}_3$, where the organic radicals $R^{1B}$-$R^{6B}$ may also be substituted by halogens and two geminal or vicinal radicals $R^{1B}$-$R^{6B}$ may also be joined to form a five- or six- membered ring and $R^{7B}$ are each, independently of one another hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{7B}$ may also be joined to form a five- or six-membered ring.

5. The monocyclopentadienyl complex as claimed in claim 1, wherein

Z is

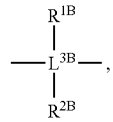

where $L^{3B}$ are each independently of one another, carbon or silicon, $R^{1B}$-$R^{2B}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl radical and 6-20 carbon atoms in the aryl radical or $SiR^{7B}_3$, where the organic radical $R^{1B}$-$R^{2B}$ may also be substituted by halogens and two radicals $R^{1B}$-$R^{2B}$ may also be joined to form a five- or six-membered ring and $R^{7B}$ are each, independently of one another hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl radical and 6-20 carbon atoms in the aryl radical and two radicals $R^{7B}$ may also be joined to form a five- or six-membered ring.

6. The monocyclopentadienyl complex as claimed in claim 1 wherein $E^{1A}$-$E^{5A}$ are each carbon or at most one $E^{1A}$ to $E^{5A}$ is phosphorus.

7. A monocyclopentadienyl complex as claimed in claim 1, wherein at least two vicinal radicals $R^{1A}$-$R^{5A}$ are joined to form a 5-membered heterocycle which contains at least one atom from group 15 or 16 of the Periodic Table.

8. A monocyclopentadienyl complex as claimed in claim 1 wherein at least two vicinal radicals $R^{1A}$-$R^{5A}$ are joined to form a 5-membered heterocycle which contains one atom from group 15 or 16 of the Periodic Table.

* * * * *